(12) United States Patent
Won et al.

(10) Patent No.: US 10,809,196 B2
(45) Date of Patent: Oct. 20, 2020

(54) QUENCHER CONTAINING WATER SOLUBLE POLYMER-CONJUGATED NANOMATERIAL AND USE THEREOF

(71) Applicant: LEMONEX INC., Seoul (KR)

(72) Inventors: Cheolhee Won, Seoul (KR); Dal-Hee Min, Seoul (KR)

(73) Assignee: LEMONEX INC., Seoul (KR)

(*) Notice: Subject to any disclaimer, the term of this patent is extended or adjusted under 35 U.S.C. 154(b) by 346 days.

(21) Appl. No.: 15/765,409

(22) PCT Filed: Jun. 15, 2016

(86) PCT No.: PCT/KR2016/006355
§ 371 (c)(1),
(2) Date: Apr. 2, 2018

(87) PCT Pub. No.: WO2017/057823
PCT Pub. Date: Apr. 6, 2017

(65) Prior Publication Data
US 2018/0306718 A1 Oct. 25, 2018

(30) Foreign Application Priority Data

Oct. 2, 2015 (KR) .................. 10-2015-0139174

(51) Int. Cl.

| G01N 33/53 | (2006.01) |
|---|---|
| C12Q 1/70 | (2006.01) |
| G01N 33/533 | (2006.01) |
| G01N 21/64 | (2006.01) |
| C12N 15/115 | (2010.01) |
| G01N 33/58 | (2006.01) |
| C12Q 1/6888 | (2018.01) |
| C12Q 1/6818 | (2018.01) |
| C08B 37/02 | (2006.01) |
| C08B 37/08 | (2006.01) |
| C12N 1/20 | (2006.01) |
| G01N 33/574 | (2006.01) |
| A61K 49/00 | (2006.01) |
| B82Y 30/00 | (2011.01) |

(52) U.S. Cl.
CPC ....... *G01N 21/6428* (2013.01); *C08B 37/003* (2013.01); *C08B 37/0021* (2013.01); *C12N 1/20* (2013.01); *C12N 15/115* (2013.01); *C12Q 1/6818* (2013.01); *C12Q 1/6888* (2013.01); *C12Q 1/70* (2013.01); *G01N 33/53* (2013.01); *G01N 33/533* (2013.01); *G01N 33/574* (2013.01); *G01N 33/58* (2013.01); *A61K 49/0017* (2013.01); *B82Y 30/00* (2013.01); *G01N 2021/6432* (2013.01); *G01N 2021/6439* (2013.01); *Y02A 50/30* (2018.01)

(58) Field of Classification Search
CPC .. G01N 21/6428; G01N 33/53; G01N 33/533; G01N 33/5308; G01N 33/582; G01N 33/58; C12G 1/6888; C12G 1/6818
See application file for complete search history.

(56) References Cited

U.S. PATENT DOCUMENTS

| 2014/0100124 A1 | 4/2014 | Wylie et al. |
| 2015/0080251 A1 | 3/2015 | Min et al. |

FOREIGN PATENT DOCUMENTS

| CN | 102603896 A | 7/2012 |
|---|---|---|
| KR | 10-2013-0017271 A | 2/2013 |
| KR | 10-2014-0014443 A | 2/2014 |
| KR | 10-2014-0048008 A | 4/2014 |
| KR | 10-2014-0119633 A | 10/2014 |
| KR | 10-1496671 B1 | 3/2015 |
| KR | 10-1554173 B1 | 9/2015 |

OTHER PUBLICATIONS

Xiang-Ling Li et al. "On-chip selective capture of cancer cells and ultrasensitive fluorescence detection of survivin mRNA in a single living cell", Lab on a Chip, vol. 13, pp. 3868-3875, 2013.
Li Gao et al. "Highly sensitive detection for proteins using graphene oxide-aptamer based sensors", Nanoscale, vol. 7, pp. 10903-10907, 2015.
Shuai Zhang et al., "In vitro and in vivo behaviors of dextran functionlized graphen", Carbon, vol. 49, pp. 4040-4049, 2011.
Yali Xie et al. "Determination of Lysozyme by Graphene Oxide-Polyethylene Glycol-Based Fluorescence Resonance Energy Transfer", Analytical Letters, vol. 50, pp. 148-160, 2017.
European Search Report for EP16851971.8 dated Feb. 26, 2019 from European patent office in a counterpart European patent application.
Office action dated Feb. 5, 2019 from Japan Intellectual Property Office in a counterpart Japanese Patent Application No. 2018-516666 (all the cited references are listed in this IDS.) (English translation is submitted herewith).
Office action dated Oct. 8, 2019 from China Patent Office in a counterpart China Patent Application No. 201680057579.2 (all the cited references are listed in this IDS.) (English translation is also submitted herewith.).
Yali Xie, "Study on Preparation of Functionalized Graphene Oxide and Its Application to Polypeptide and Protein", China Masters' Theses Fulltext Database, vol. Engineering Science and Technology, No. 2014/09, B014-28, 2014 (English translation is submitted herewith).
Haifeng Dong et al., "The use of polyethylenimine-grafted graphene nanoribbon for cellular delivery of locked nucleic acid modified molecular beacon for recognition of microRNA", BioMaterials, 32: pp. 3875-3882, 2011.

(Continued)

*Primary Examiner* — Christopher Adam Hixson
(74) *Attorney, Agent, or Firm* — The PL Law Group, PLLC

(57) ABSTRACT

A quencher containing water-soluble polymer-conjugated nanomaterial effectively quenches the fluorescence of a fluorescent material-conjugated probe. In addition, a composition including the quencher and a fluorescent material-conjugated probe can detect a target material existing at a low concentration, and thus can be favorably used as a composition or kit for providing information necessary for the detection of a biomaterial or the diagnosis of a disease.

20 Claims, 18 Drawing Sheets

Specification includes a Sequence Listing.

(56) References Cited

OTHER PUBLICATIONS

Dinggeng He et al., "Nanometer-sized manganese oxide-quenched fluorescent oligonucleotides: an effective sensing platform for probing biomolecular interactions", Chem. Commun., vol. 50, pp. 11049-11052, 2014.
International Search Report for PCT/KR2016/006355.
Haixin Chang et al. "Graphene Fluorescence Resonance Energy Transfer Aptasensor for the Thrombin Detection", Analytical Chemistry, vol. 82, No. 6, pp. 2341-2346, 2010.
Huawen Hu et al., "Organic Liquids-Responsive Beta-Cyclodextrin-Functionalized Graphene-Based Fluorescence Probe: Label-Free Selective Detection of Tetrahydrofuran", Molecules 2014, 19, 7459-7479; doi:10.3390/molecules19067459.
Zhenbao Liu et al. "Fluorescent sensors using DNA-functionalized graphene oxide", Analytical and Bioanalytical Chemistry, 406:6885-6902, DOI 10.1007/s00216-014-7888-3, Jul. 2014.
Office action dated Aug. 30, 2017 from Korean Patent Office in a counterpart Korean Patent Application No. 10-2016-0074537 (all the cited references are listed in this IDS.) (English translation is also submitted herewith.).
Office action dated Aug. 6, 2019 from Japan Intellectual Property Office in a counterpart Japanese Patent Application No. 2018-516666 (all the cited references are listed in this IDS.) (English translation is submitted herewith).
Jiayan Luo et al. "Graphene Oxide Nanocolloids", J. Am Chem. Soc., vol. 132, pp. 17667-17669, 2010.
Dinggeng He et al., "A sensitive turn-on fluorescent probe for intracellular imaging of glutathione using single-layer MnO2 nanosheet-quenched fluorescent carbon quantum dots", Chem. Commun., vol. 51, pp. 14764-14767, 2015.

Scale bar is 20 μm.

Scale bar is 100 μm.

QUENCHER CONTAINING WATER SOLUBLE POLYMER-CONJUGATED NANOMATERIAL AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/006355, filed Jun. 15, 2016, which claims priority to the benefit of Korean Patent Application No. 10-2015-0139174 filed in the Korean Intellectual Property Office on Oct. 2, 2015, the entire contents of which are incorporated herein by reference.

TECHNICAL FIELD

The present invention relates to a quencher containing a water-soluble polymer-conjugated nanomaterial and a use thereof.

BACKGROUND ART

Methods for detecting a specific nucleic acid (DNA or RNA) or protein are critical techniques in the field of scientific research. As a specific nucleic acid or protein can be detected, researchers were able to determine which genetic or biological marker is a marker indicating the health condition of a human. According to such methods for detecting a nucleic acid or protein, modification of a pathogenic gene present in a sample or the expression of a specific gene present in a sample may be found.

However, an organic or inorganic polymer, such as graphene oxide, having a planar structure filled with a two-dimensional lattice and derivatives thereof can transfer electrons. Such electron transfer is caused by physical properties such as the crystalline and lattice structures of the polymer. Particularly, the fluorescent signal of an organic fluorescent dye may be quenched by fluorescence resonance energy transfer (FRET).

Therefore, a change in the fluorescent signal of a fluorescent dye-conjugated nucleic acid polymer may be observed using the physical properties of a material such as graphene oxide, and thus a biomaterial such as a nucleic acid or a protein may be detected (Korean Patent Publication No. 10-1496671). In addition, a method for detecting the activity of a fluorescence analysis-based enzyme using such a material was developed (Korean Patent Publication No. 10-1554173). Recently, techniques using such a material have been used to observe a gene or protein of a pathogen present in a sample, and therefore have become significant in the initial research on a disease and an illness.

However, while such a detection method using graphene oxide is simple, it can be greatly influenced by an amount of a target material included in a sample, and since the size distribution of nucleic acid polymers used in detection is not uniform, an error range is wide. In addition, in an in vitro environment for in vitro diagnosis, the polymers are instable, and thus reproducibility is reduced.

SUMMARY

It is an object of the present invention to provide a quencher containing water-soluble polymer-conjugated nanomaterial and a composition including the quencher and a fluorescent material-conjugated probe. In addition, it is another object of the present invention to provide a method for providing information necessary for the diagnosis of a disease using the composition.

To achieve the objects, the present invention provides a quencher containing a water-soluble polymer-conjugated nanomaterial.

In addition, the present invention provides a composition including the quencher and a fluorescent material-conjugated probe.

In addition, the present invention provides a method for providing information necessary for the diagnosis of a disease, the method including: preparing a mixture by mixing the composition with an isolated sample; measuring a fluorescence level of the mixture; and comparing the resulting level with a fluorescence level of a normal control sample.

In addition, the present invention provides a kit including the quencher and a fluorescent material-conjugated probe.

A quencher containing a water-soluble polymer-conjugated nanomaterial of the present invention effectively quenches the fluorescence emitted from a fluorescent material-conjugated probe. In addition, the water-soluble polymer-conjugated nanomaterial is stably bound with the fluorescent material-conjugated probe. Moreover, in the presence of a target material, as the probe is bound to the target material, the probe can be easily released from the water-soluble polymer-conjugated nanomaterial, and thus the target material can be effectively detected. Therefore, a composition including the quencher and the fluorescent material-conjugated probe can also detect a target material present at a low concentration. For this reason, the composition can be effectively used as a composition or kit for providing information necessary for the detection of a biomaterial or the diagnosis of a disease.

BRIEF DESCRIPTION OF THE DRAWINGS

FIG. 6A), or GON which is surface-modified with PEG and polyethyleneimine (PEI) (PEG-PEI-GON; FIG. 6B).

DETAILED DESCRIPTION

Figure 1:
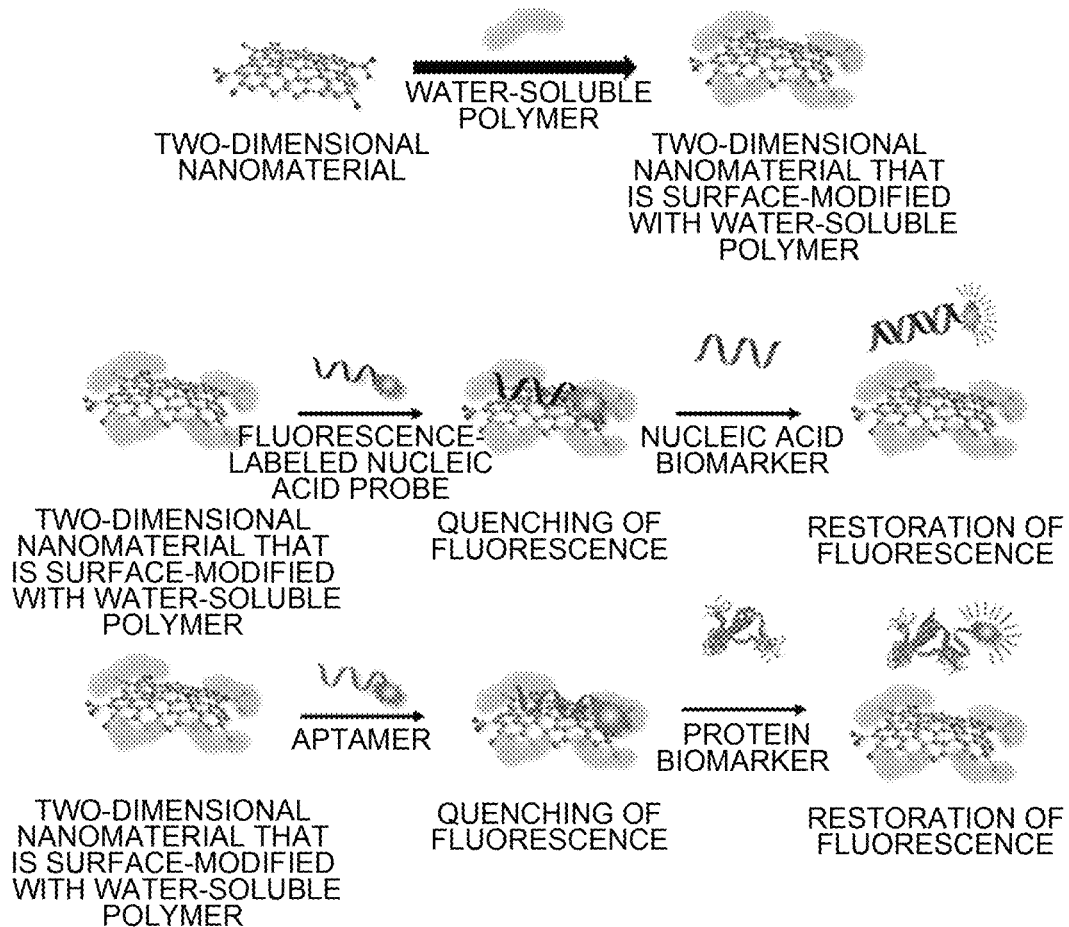
FIG. 1 is a schematic diagram illustrating a method for preparing a water-soluble polymer-conjugated nanomaterial and a method for detecting a biomaterial using the material prepared thereby.

Hereinafter, the present invention will be described in detail.

In one aspect, the present invention provides a quencher containing a water-soluble polymer-conjugated nanomaterial.

The term "water-soluble polymer" used herein refers to a resin or polymer that can be dissolved in water or dispersed as fine particles in water. The water-soluble polymer may be a natural polymer, semi-synthetic polymer or synthetic polymer. The water-soluble polymer that can be used in the present invention may have a molecular weight of 1 to 20 kDa, 5 to 15 kDa or 8 to 12 kDa. In one embodiment, the molecular weight of the water-soluble polymer may be 10 kDa.

The water-soluble polymer may be selected from the group consisting of chitosan and a derivative thereof, a chitosan salt, dextran and a derivative thereof, hyaluronic acid and a derivative thereof, a hyaluronate, pectin and a derivative thereof, pectin salt, an alginate and a derivative thereof, alginic acid, agar, a galactomannan and a derivative thereof, a galactomannan salt, xanthan and a derivative thereof, a xanthan salt, β-cyclodextrin and a derivative thereof, a β-cyclodextrinate, polyethylene glycol (PEG), polyethyleneimine (PEI) and a combination thereof. In an embodiment, the water-soluble polymer may be selected from the group consisting of dextran, polyethylene glycol, polyethyleneimine and a combination thereof.

The term "nanomaterial" used herein refers to a nanoscale material. Due to a small size, the nanomaterial may easily pass through a cell membrane. The nanomaterial may be in a sheet or particle shape. The sheet may consist of a single layer or multiple layers. In addition, the sheet conformation may include a flat or curved surface, and may be present in various forms. In one embodiment, the nanomaterial may be a two-dimensional single-layer sheet-type nanomaterial. In addition, the particle shape may include various forms such as a sphere, an oval, a rod, and a polygon.

A particle size of the nanomaterial may be approximately 10 to 500, 10 to 200, 10 to 150, 10 to 100, 10 to 50, 20 to 200, 20 to 150, 20 to 100, 20 to 50, 30 to 200, 30 to 150, 30 to 100, 30 to 50, 50 to 200, 50 to 150, 50 to 100, 50 to 80, 60 to 200, 60 to 100, 60 to 80, 80 to 200, 80 to 150, 80 to 100, 90 to 200, 90 to 150, or 90 to 100 nm, but the present invention is not limited thereto. In one embodiment of the present invention, the particle size of the nanomaterial is preferably 50 to 80, 90 to 200, 90 to 150 or 80 to 100 nm. Here, the particle size is an average of experimental values measured using dynamic light scattering or sizes shown in AFM or STEM images, referring to a value obtained under the assumption that the nanomaterial is spherical or circular.

The nanomaterial may be prepared as a carbon nanomaterial or manganese dioxide. Here, the carbon nanomaterial may be selected from the group consisting of NGO and a derivative thereof, reduced graphene oxide and a derivative thereof, GON and a combination thereof. In one embodiment, the nanomaterial may be NGO, GON or manganese dioxide.

The term "quencher" used herein refers to a material that absorbs fluorescence energy of a material emitting fluorescence by absorbing light or a wavelength. A quenching effect occurs due to the interaction between a fluorescent material and a nanomaterial. The quenching effect usually occurs when the fluorescent material is located a short distance, for example, approximately 10 nm or less, from the nanomaterial. Here, the fluorescent material serves as an energy donor, and the nanomaterial serves as an energy acceptor.

The quencher may be prepared by modifying the surface of a nanomaterial by a water-soluble polymer. Here, the water-soluble polymer and the nanomaterial may be conjugated by a chemical or physical bond. The chemical bond may be an amide bond, an ester bond or an ether bond, but the present invention is not limited thereto. In addition, the chemical bond may be achieved through a crosslinker. In one embodiment, the water-soluble polymer and the nanomaterial may be conjugated by EDC coupling. In addition, the physical bond may be an electrostatic attraction, a hydrogen bond, or a Van deer Waals bond, but the present invention is not limited thereto. In addition, such a nanomaterial which is surface-modified with a water-soluble polymer may be improved in dispersibility, stability and biocompatibility.

In addition, in another aspect, the present invention provides a composition including the quencher and a fluorescent material-conjugated probe.

The term "probe" used herein refers to a material capable of specifically binding to a target material. The probe may be any one selected from the group consisting of an antibody, a nucleic acid, a peptide, a protein and a combination thereof. In addition, any material that is known as a material with high affinity to a target material can be used. In an embodiment, the antibody may specifically bind to an epitope of a target protein to detect the target material. In addition, when the nucleic acid has a complementary sequence to the sequence of a nucleic acid of the target material, the nucleic acid may bind to a target base sequence to detect the target material. In addition, the peptide may specifically bind to a receptor or ligand expressed on a cell surface to detect the target material.

The nucleic acid may be any one selected from the group consisting of DNA, RNA, mRNA, miRNA, non-coding RNA, double helix RNA, double helix DNA, a DNA-based enzyme, a deoxyribozyme, an aptamer, a peptide nucleic acid (PNA), a locked nucleic acid (LNA) and a combination thereof.

Here, while the nucleic acid may consist of 10 to 50, 10 to 30, 12 to 28, 15 to 25, or 18 to 22 bases, if the nucleic acid is capable of complementary binding to a target nucleic acid sequence, there is no limit to the number of bases. In one embodiment, the nucleic acid may consist of 15 to 22 bases. In one embodiment of the present invention, the nucleic acid may be any one selected from the group consisting of SEQ ID NOs: 1 to 20.

A fluorescent material binds to the probe according to the present invention. The fluorescent material is present in a quenched state by absorption of fluorescence energy by a water-soluble polymer-conjugated nanomaterial, and when the probe is released from the nanomaterial due to specific binding to the target material, fluorescence is emitted. The fluorescent material may bind to one end or the middle of the probe. When the probe is a nucleic acid, the fluorescent material may be located at the 5' or 3' position of the nucleic acid or in the nucleic acid. When the probe is a peptide, the fluorescent material may bind to the N- or C-terminal of the peptide, or in the peptide. The fluorescent material may bind to the probe directly or through a crosslinker.

The fluorescent material may be selected from the group consisting of fluorescein, fluorescein chlorotriazinyl, rhodamine green, rhodamine red, tetramethylrhodamine, fluorescein isothiocyanate (FITC), Oregon green, an Alexa Fluor dye, carboxyfluorescein (FAM), 6-carboxy-4',5'-dichloro-2',7'-dimethoxyfluorescein (JOE), carboxy-X-rhodamine (ROX), 6-carboxy-2',4,4',5',7,7'-hexachlorofluorescein (HEX), Texas red (sulforhodamine 101 acid chloride), 6-carboxy-2',4,7',7-tetrachlorofluorescein (TET), tetramethylrhodamine-isothiocyanate (TRITC), carboxytetramethylrhodamine (TAMRA), a cyanine-based dye, a thiodicarbocyanine dye, and a combination thereof. The cyanine-based dye may be selected from the group consisting of Cy3, Cy5, Cy5.5, Cy7 and a combination thereof.

The quencher may detect one or more targets. To detect one or more targets, the nanomaterial may include two or more different probes. Here, each probe may include a different fluorescent material. Here, each probe may bind a different target material so as to detect a different target material.

In addition, the composition may be used to provide information necessary for the detection of a biomaterial or the diagnosis of a disease. The disease may be cancer, an infectious disease, an inflammatory disease, or a genetic disease, and in one embodiment, the disease is preferably cancer or an inflammatory disease.

The cancer may be selected from the group consisting of breast cancer, lung cancer, liver cancer, pancreatic cancer, stomach cancer, colorectal cancer, bone cancer, skin cancer, brain tumors, sarcoma, eye cancer, bone marrow cancer, blood cancer and a combination thereof. Meanwhile, the infectious disease may be caused by an infection of any one selected from the group consisting of bacteria, fungi, viruses, parasites and a combination thereof. Here, the bacteria may be enterobacteria or enterococci. Examples of the bacteria include *Pseudomonas aeruginosa*, *Staphylococcus aureus* and *Acinetobacter baumannii*. In one embodiment of the present invention, the bacteria are preferably *Pseudomonas aeruginosa* or *Staphylococcus aureus*.

Examples of the viruses may include a double-stranded DNA virus, a single-stranded DNA virus, a double-stranded RNA virus, a positive-sense single-stranded RNA virus, a negative-sense single-stranded RNA virus, a single-stranded RNA retrovirus and a double-stranded DNA retrovirus. In one embodiment of the present invention, the virus may be selected from the group consisting of cytomegalovirus, Dengue virus and a combination thereof.

In still another aspect, the present invention provides a method for providing information necessary for the diagnosis of a disease, the method including: mixing the composition including the quencher and the fluorescent material-conjugated probe with an isolated sample; measuring a fluorescence level of the mixture; and comparing the resulting level with a fluorescence level of a normal control sample.

The quencher and the fluorescent material-conjugated probe, which are included in the composition, are as described above. In addition, the sample may be a sample isolated and discharged from a diagnosis target, and may be cells, a cell culture medium, tissue, saliva, urine, feces, semen, blood, plasma or serum. In addition, a normal control sample refers to a sample isolated and discharged from a normal person without a disease.

The method according to the present invention may be used to detect a biomaterial such as a nucleic acid or protein, or to diagnose a disease as described above. Here, the fluorescence may be determined by measuring light emitted while being released by specifically contacting or binding a fluorescent material quenched by a nanomaterial with a target material. To measure the fluorescence level, flow cytometry, fluorescence-activated cell sorting (FACS), or a method for analyzing a fluorescent signal or an image may be used.

In yet another aspect, the present invention provides a kit including the quencher and the fluorescent material-conjugated probe. The quencher and the fluorescent material-conjugated probe, which are included in the composition, are as described above. The kit may be used to detect a biomaterial such as a nucleic acid or protein, or to diagnose a disease as described above.

Hereinafter, the present invention will be fully described with reference to the following examples. However, the following examples are merely provided to exemplify the present invention, and the present invention is not limited by the examples.

I. Preparation of Two-Dimensional Nanomaterial

Example 1. Preparation of Graphene Oxide Nanocolloid (GON)

4 g of $K_2S_2O_8$ and 4 g of $P_4O_{10}$ were added to 50 ml of $H_2SO_4$ and dissolved while stirring. 2 g of graphite nanofiber was added to the resulting solution, and heated at 90° C. for 16 hours. The heated mixture was cooled to room temperature, 250 ml of distilled water was added thereto, followed by filtration with a paper filter (Whatman-GE Healthcare, USA). The purified mixture was washed with distilled water twice or more and dried in air.

1.5 g of the dry powder-type graphite nanofiber was added to 250 ml of $H_2SO_4$, 10 g of $KMnO_4$ was slowly added thereto, and reacted while stirring. Here, a reaction temperature did not exceed 10° C. The reaction products were warmed up in 35° C. distilled water for further reaction while stirring for 6 hours. After the reaction, 1,000 ml of distilled water was added, and here, the temperature was maintained at 55° C. or less. 50 ml of $H_2O_2$ was added to the mixture to allow a reaction, and the resulting mixture was centrifuged at 10,000 rpm for 30 minutes, thereby obtaining a pellet. The obtained pellet was washed with 3.4% (w/w) HCl and acetone three times or more using a centrifuge.

Figure 2:
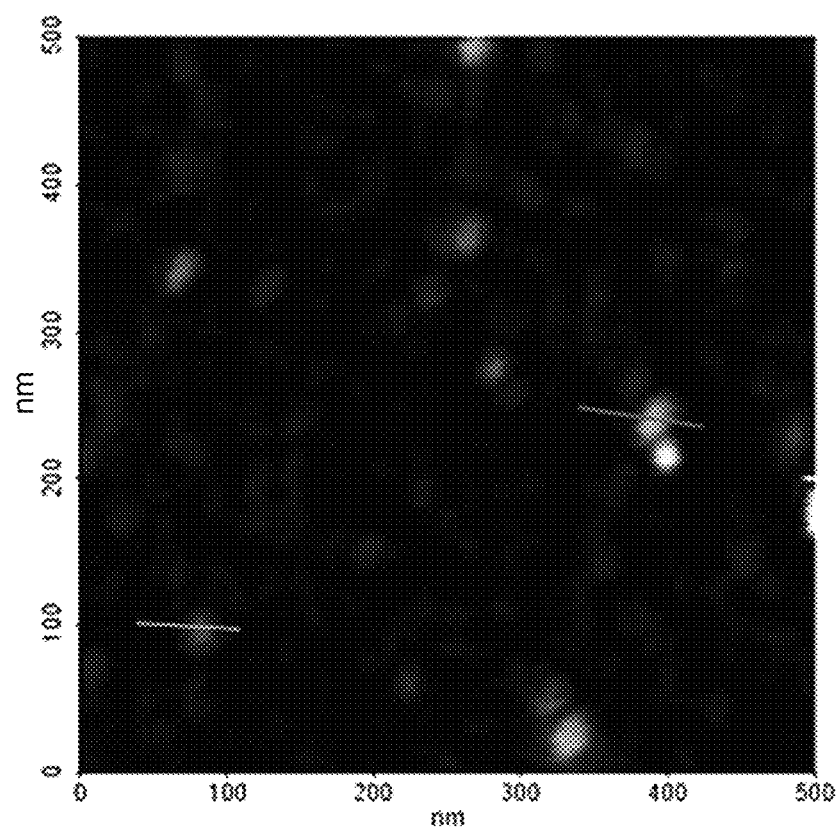
FIG. 2 is an atomic force microscope (AFM) image of a graphene oxide nanocolloid (GON) prepared in an example.

The acetone contained in the finally-obtained brownish supernatant was removed under vacuum, and distilled water was added to the remaining solution to adjust the final concentration to 1 mg/ml, followed by vortexting for complete suspension. The collected product was purified and neutralized using a 10,000 Da dialysis membrane, and the final product was lyophilized to obtain powder-type GON. The obtained GON was observed using AFM, and the result is shown in FIG. 2. As shown in FIG. 2, GON with a size of 100 nm or less and a thickness of 2 nm or less was obtained.

Example 2. Preparation of Manganese Dioxide ($MnO_2$)

Distilled water was added to a solution of 32 ml of sodium dodecyl sulfate (SDS) and 1.6 ml of $H_2SO_4$ to adjust the final volume to 300 ml. The resulting solution was heated at 95° C. for 15 minutes, and then 3.2 ml of a $KMnO_4$ solution was rapidly added thereto. Afterward, heating was continued for 60 minutes, and a dark brown manganese dioxide sheet was obtained.

Figure 3A:
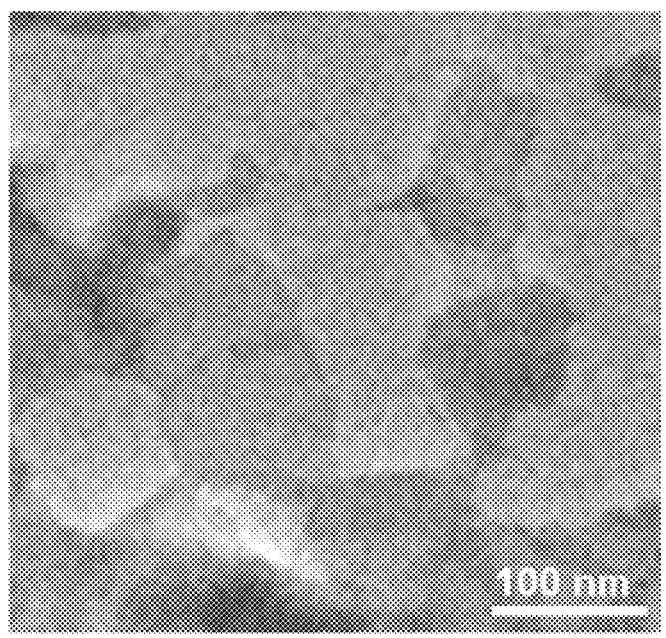
FIGS. 3A and 3B include scanning-transmission electron microscope (STEM; a) and AFM (b) images of two-dimensional nanomaterial, manganese dioxide, prepared in an example.
Figure 3B:
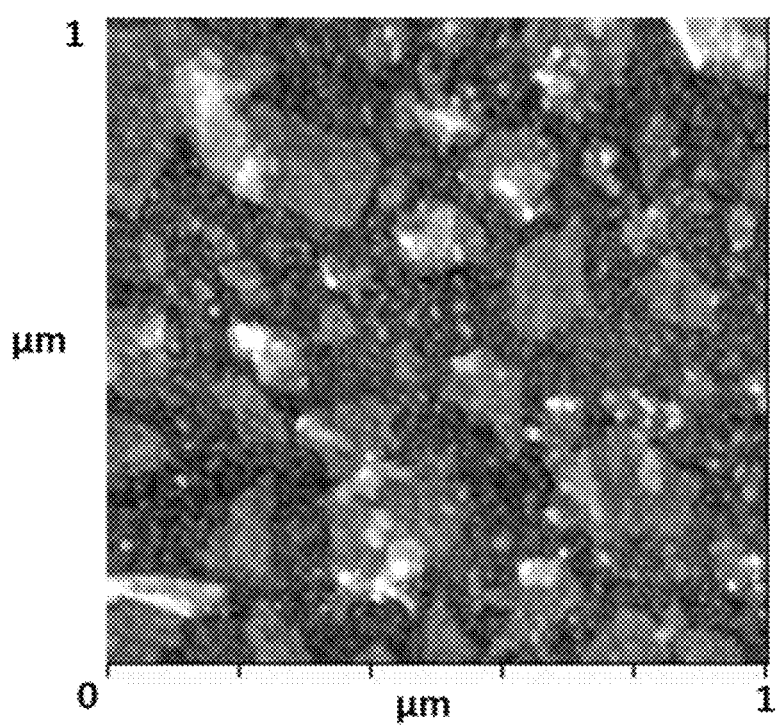

Triple distilled water and an alcohol were added at a volume ratio of 1:1 to the obtained manganese dioxide sheet, and centrifuged at 12,000 rpm, thereby obtaining a pellet. In addition, centrifugation was performed twice under the same conditions to allow the obtained product to be resuspended in triple distilled water, thereby obtaining the final product. The obtained $MnO_2$ was observed by STEM and AFM, and the result is shown in FIGS. 3A and 3B. As shown in FIG. 3B, $MnO_2$ with a size of 200 nm or less and a thickness of 2 nm or less was obtained.

Example 3. Preparation of Nano Graphene Oxide (NGO)

0.5 g of $Na_2NO_3$ was added to 23 ml of $H_2SO_4$ and dissolved while stirring. 0.5 g of graphite nanofiber was added to the resulting solution, and then 3 g of $KMnO_4$ was slowly added thereto while stirring to allow a reaction. Here, a reaction temperature did not exceed 10° C. The reaction products were warmed up in 35° C. distilled water for further reaction while stirring for 1 hour, and then were further reacted at 90° C. for 30 minutes. After the reaction, 1 ml of distilled water was added, and the temperature was maintained at 55° C. or less. 3 ml of $H_2O_2$ was added to the reaction products to allow a reaction, cooled to room temperature, and then 250 ml of distilled water added thereto. After the resulting solution was filtered using a paper filter, a filtrate obtained thereby was washed with distilled water twice or more and dried in air.

Figure 4A:
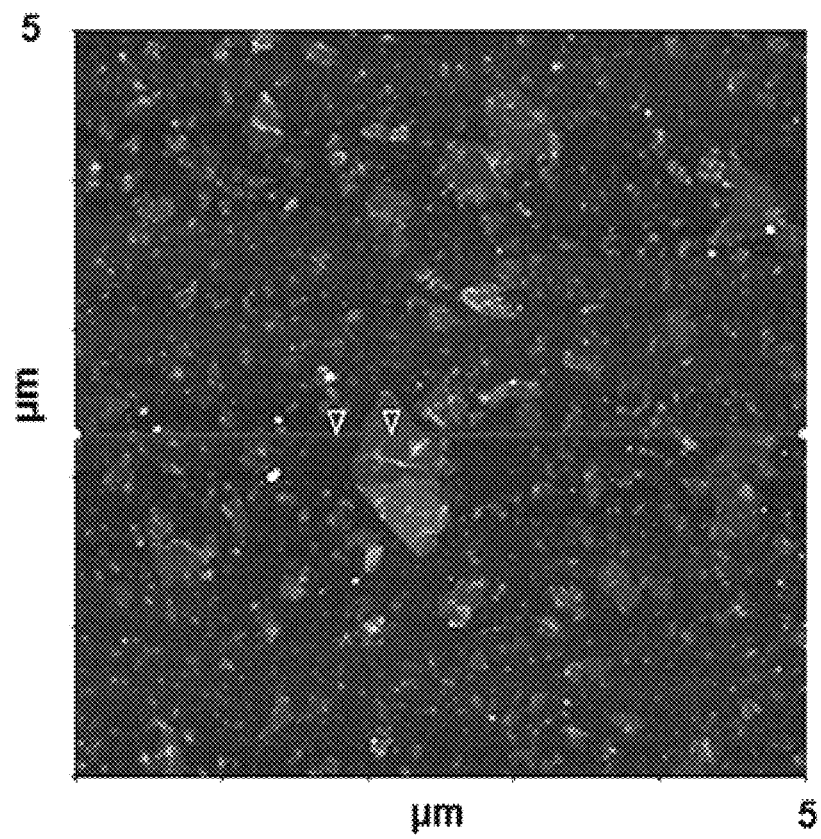
FIGS. 4A and 4B are AFM images of nano graphene oxide (NGO) prepared in an example.
Figure 4B:
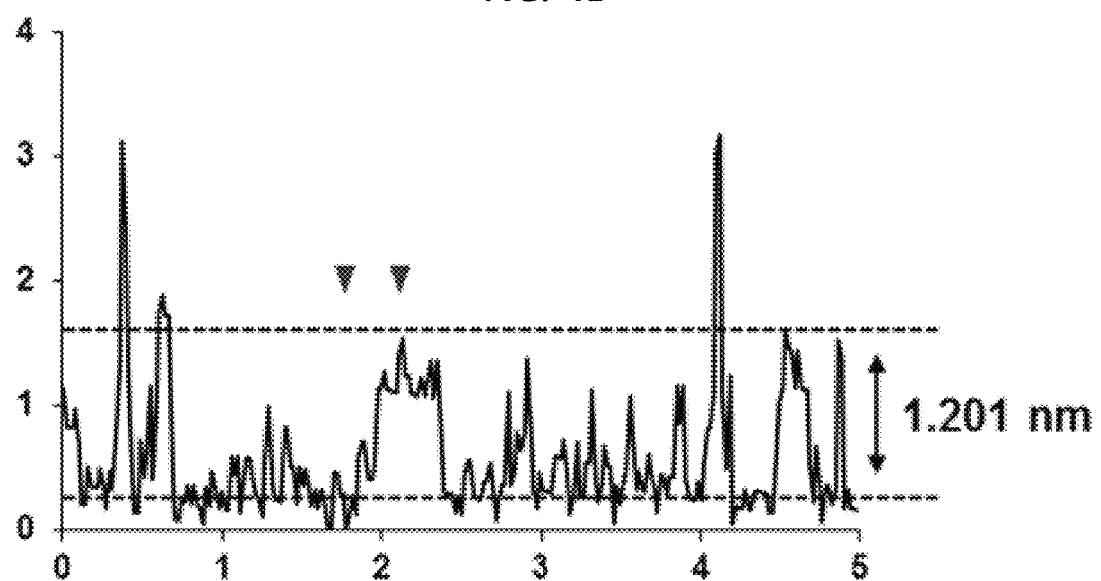

To prepare graphene oxide (GO), 50 ml of 9M NaOH was added to 10 mg/ml of a graphene oxide solution, followed by tip-sonication for 90 minutes. The graphene oxide was purified and neutralized using a 3,800 Da dialysis membrane, and the final product was lyophilized to obtain powder-type NGO. The obtained NGO was observed using AFM, and the result is shown in FIGS. 4A and 4B. As shown in FIGS. 4A and 4B, NGO with a size of 200 nm or less and a thickness of 1.5 nm or less was obtained.

II. Preparation of Two-Dimensional Nanomaterial Surface-Modified with Polymer

Example 4. Preparation of GON Surface-Modified with Dextran (DReGON)

The surface of the GON obtained in Example 1 was modified with dextran. Specifically, 50 mg of the GON was suspended in 50 ml of distilled water, and a 0.1% (w/w) dextran aqueous solution was added thereto. The mixture was subjected to ultrasonication for 30 minutes, and then reacted with 25 μl of an aqueous ammonia solution at 95° C. for 3 hours while stirring. The reaction product was washed with distilled water, isolated by centrifugation at 10,000 rpm for 30 minutes, and lyophilized, thereby obtaining a final product DReGON.

Raman analysis was performed using the obtained DReGON. Specifically, DReGON was put on a silicon wafer, and then the silicon wafer was mounted in a Raman spectrometer (LabRAM HR UV/vis/NIR), followed by spectrum analysis by irradiation of 514 nm CW laser.

Figure 5A:
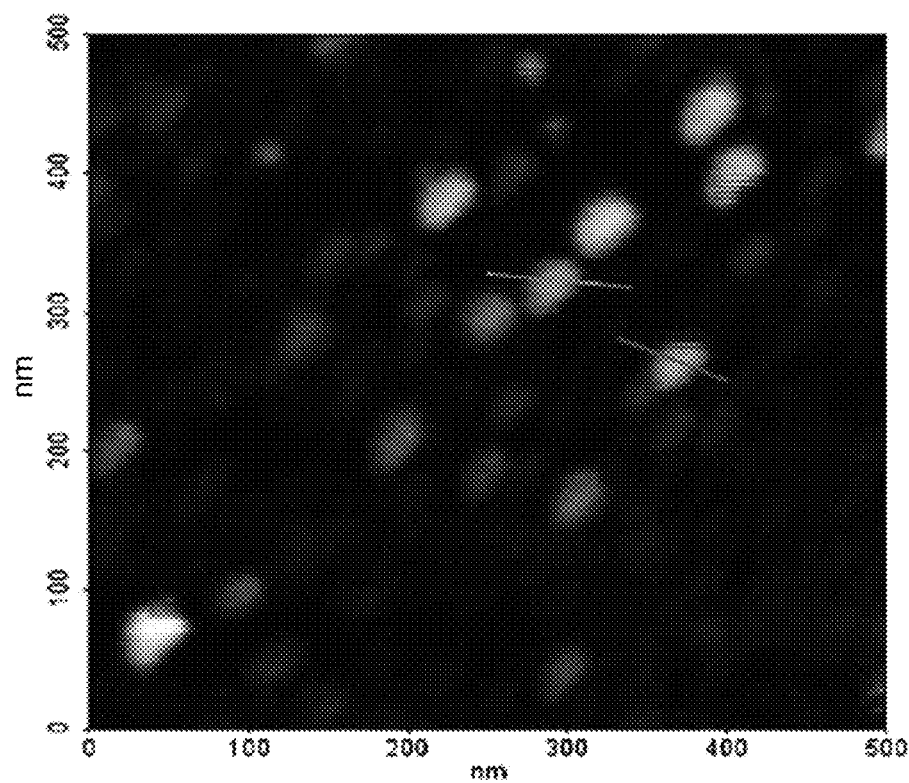
FIG. 5A includes an AFM image and FIG. 5B shows a graph representing Raman spectra of GON which is surface-modified with dextran (DReGON).
Figure 5B:
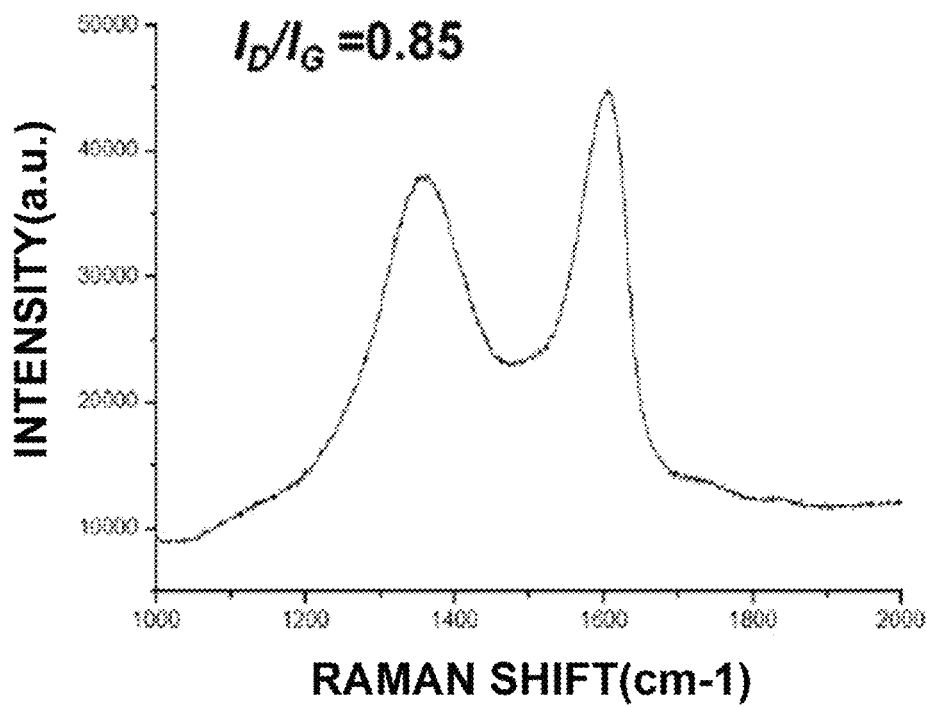

The result of observing the obtained DReGON by AFM is shown in FIG. 5A, and the result of Raman spectrum analysis is shown in FIG. 5B. As shown in FIG. 5A, DReGON with a size of 100 nm or less and a thickness of 7 nm or less was obtained. Meanwhile, as shown in FIGS. 5B, D and G peaks were observed at 1370 $cm^{-1}$ and 1600 $cm^{-1}$, respectively, and the ID/IG ratio was 0.85.

Example 5. Preparation of NGO Surface-Modified with Polyethylene Glycol (PEG)

The surface of the NGO obtained in Example 3 was modified with PEG. Specifically, 5 mg of NGO was mixed with the same amount of PEG (10 kDa), followed by bath-sonication. After adding 5 mg of 1-ethyl-3-(3-dimethylaminopropyl)carbodiimide (EDC), the bath-sonication of the mixture was further performed for 5 minutes. After being stirred for 6 hours, the mixture was purified and neutralized using a 10,000 Da dialysis membrane, and the final product was lyophilized, thereby obtaining powder-type NGO that was surface-modified with PEG (PEG-NGO).

Figure 6A:
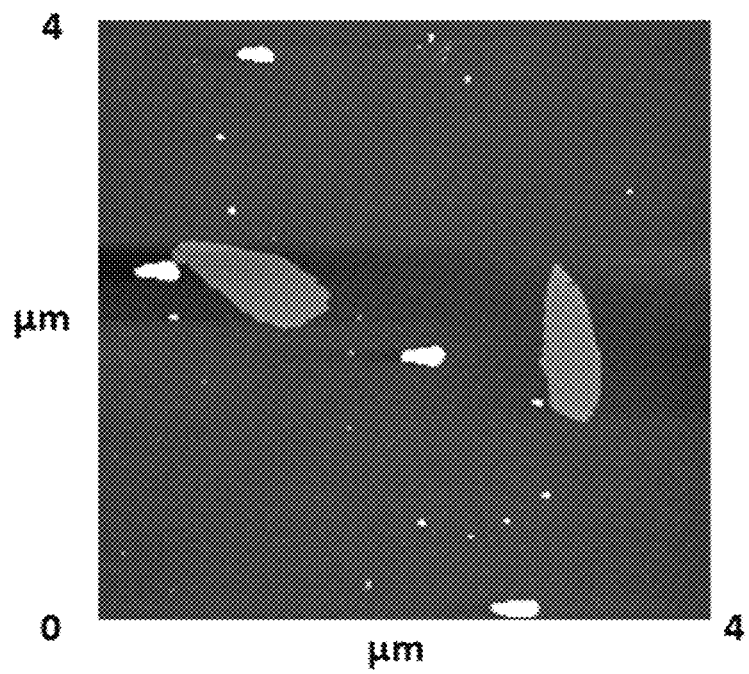
FIGS. 6A and 6B show an AFM image of NGO which is surface-modified with polyethylene glycol (PEG-NGO.

The obtained PEG-NGO was observed by AFM, and the result is shown in FIG. 6A. As shown in FIG. 6A, the PEG-NGO with a size of 200 nm or less and a thickness of 1 nm or less was obtained.

Example 6. Preparation of GON Surface-Modified with Polyethylene Glycol and Polyethyleneimine (PEI)

The surface of the GON obtained in Example 1 was modified with PEG and PEI. Specifically, 20 mg of PEG (10 kDa) was added to 10 ml of a 2 mg/ml GON solution, followed by bath-sonication for 5 minutes. By adding 20 mg of EDC, the bath-sonication of the mixture was further performed for 5 minutes. The bath-sonication was performed for 5 minutes each after the addition of 10 mg of PEI and EDC to the reaction product, followed by stirring at room temperature for 6 hours to allow uniform reactions. Afterward, the mixture was purified and neutralized using a 12,000 Da dialysis membrane, and the final product was lyophilized, thereby obtaining powder-type GON that was surface-modified with PEG and PEI (PEG-PEI-GON).

Figure 6B:
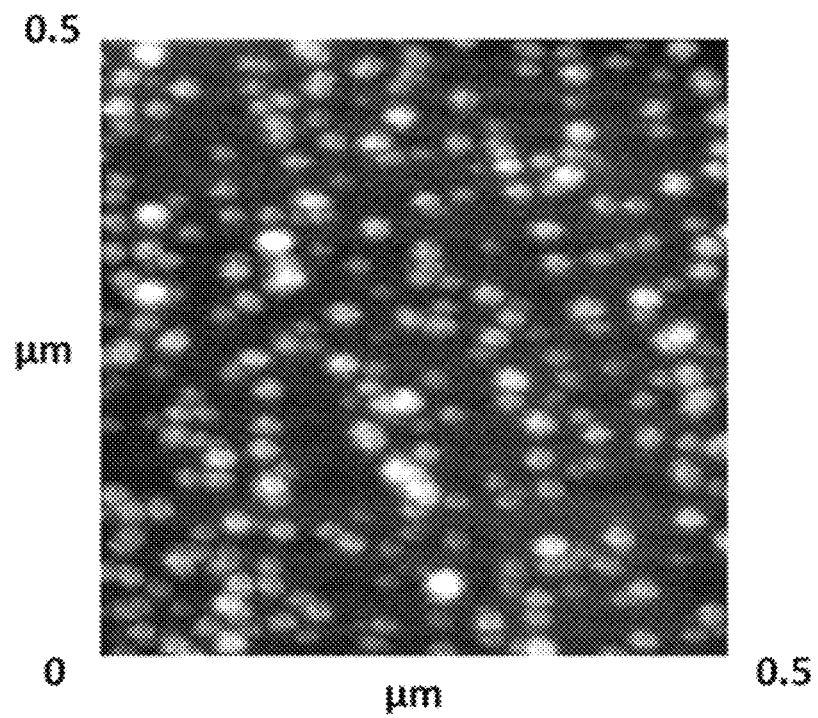

The obtained PEG-PEI-GON was observed by AFM, and the result is shown in FIG. 6B. As shown in FIG. 6B, the PEG-PEI-GON with a size of 100 nm or less and a thickness of 10 nm or less was obtained.

III. Confirmation of Preparation of Composition of Two-Dimensional Nanomaterial Surface-Modified with Polymer for Detecting Target Material Experimental Example 1. Confirmation of Preparation of Composition of Two-Dimensional Nanomaterial Surface-Modified with Polymer for Detecting Target Material Experimental Example 1-1. Confirmation of Preparation of DReGON Composition for Detecting Target Material-(1)

To confirm whether the DReGON prepared in Example 4 can be used as a composition for detecting a target material, an experiment was carried out as follows. Specifically, a peptide nucleic acid (PNA) probe for detecting a target material was prepared by requesting Panagene (Korea) to label Cy5 at the 5'-end, and include two units, as linkers, in which two carbon atoms are bound to one oxygen atom between Cy5 and the probe sequence. 1 µM of the PNA probe was added to 20 µl of nuclease-free water, and completely dissolved by being heated at 80° C. for approximately 3 minutes. 20 µl of the dissolved PNA probe was mixed with the DReGON prepared in Example 4, and reacted at room temperature for 30 minutes. Four, eight, twelve or twenty-four hours after the reaction, a fluorescence signal was measured using a fluorescence reader at Ex/Em=647/670 nm. Here, only a PNA probe was used as a control.

As a result, provided that the fluorescence signal of the PNA probe is 100%, when the PNA probe is reacted with a two-dimensional nanomaterial that is surface-modified with a polymer, the fluorescence signal is reduced to less than 5%, and therefore it was confirmed that the material forms a detection composition.

Experimental Example 1-2. Confirmation of Preparation of DReGON Composition for Detecting Target Material-(2)

Figure 7A:
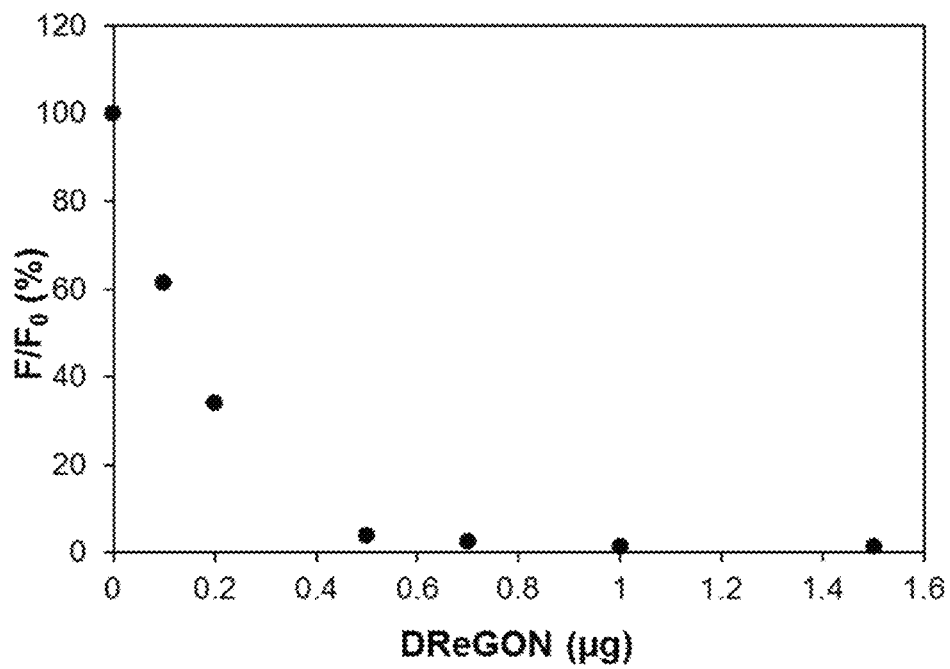
FIGS. 7A and 7B show a graph representing a fluorescent signal emitted from a mixture of DReGON and PNA-US5-2 (FIG. 7A) or PNA-DENV (FIG. 7B) as a probe, to confirm whether a detection composition is formed or not.
Figure 7B:
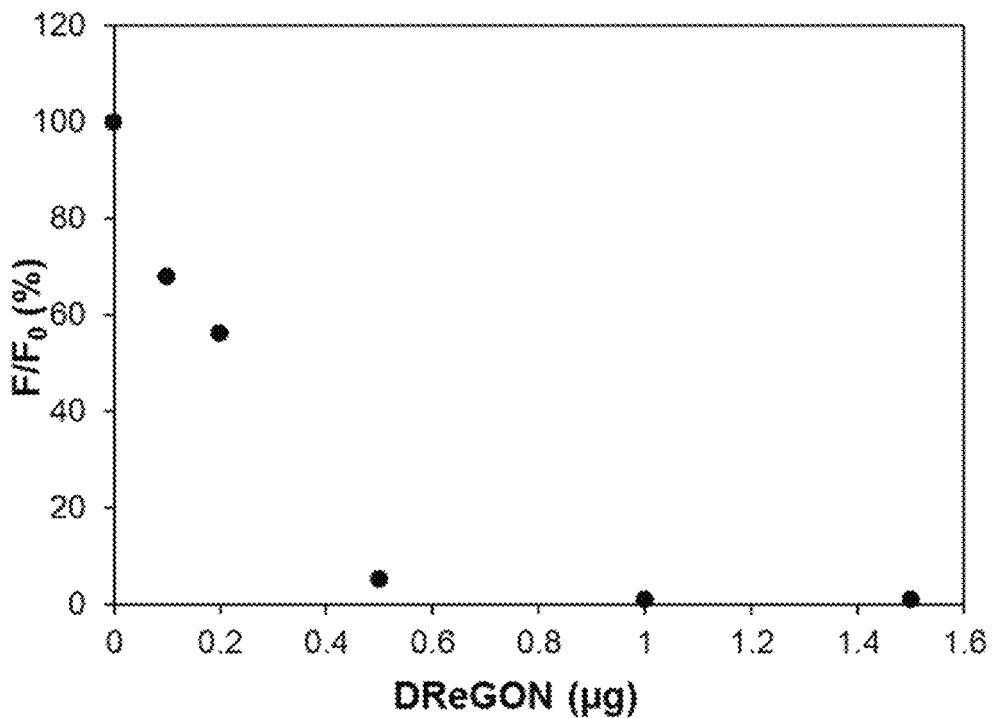

To confirm whether the DReGON prepared in Example 4 can be used as a composition for detecting a target material, an experiment was performed under the same conditions and in the same manner as in Experimental Example 1-1. Here, as a PNA probe, PNA-US5-2 or PNA-DENV listed in Table 2 was used. 10 pmol of the PNA probe was mixed with each of 0, 0.2, 0.4, 0.6, 0.8, 1.0, 1.2, 1.4 or 1.6 µg of DReGON. As a result, a value of the measured fluorescence signal is shown in FIGS. 7A and 7B. As shown in FIGS. 7A and 7B, a reduction in the fluorescence signal is dependent on a concentration of the added PNA probe, and therefore it was confirmed that the material forms a detection composition.

Figure 8A:
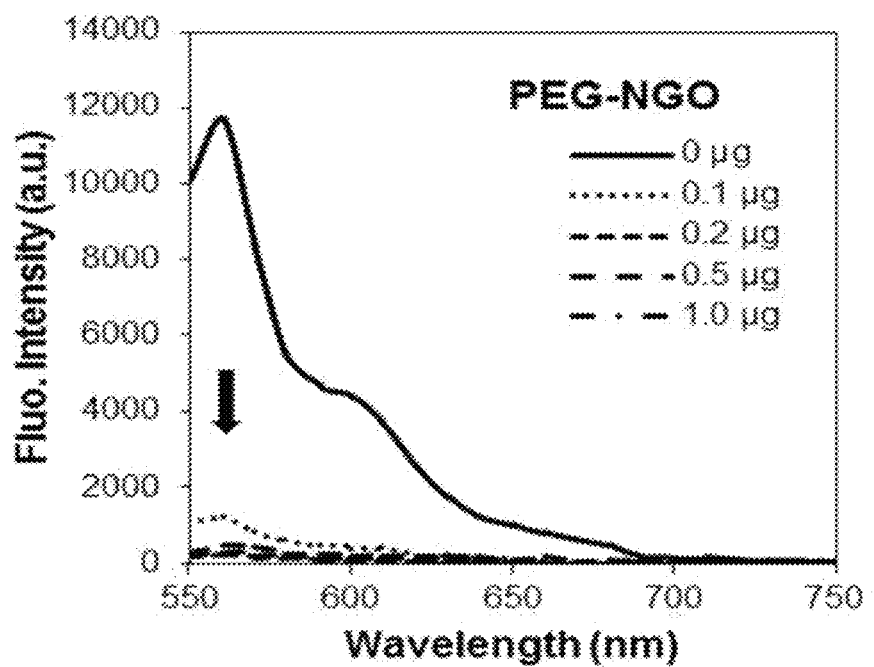
FIGS. 8A and 8B show a graph representing a fluorescent signal emitted from a mixture of PEG-NGO and PNA-Sa (FIG. 8A) or PNA-Pa (FIG. 8B) as a probe, to confirm whether a detection composition is formed or not.
Figure 8B:
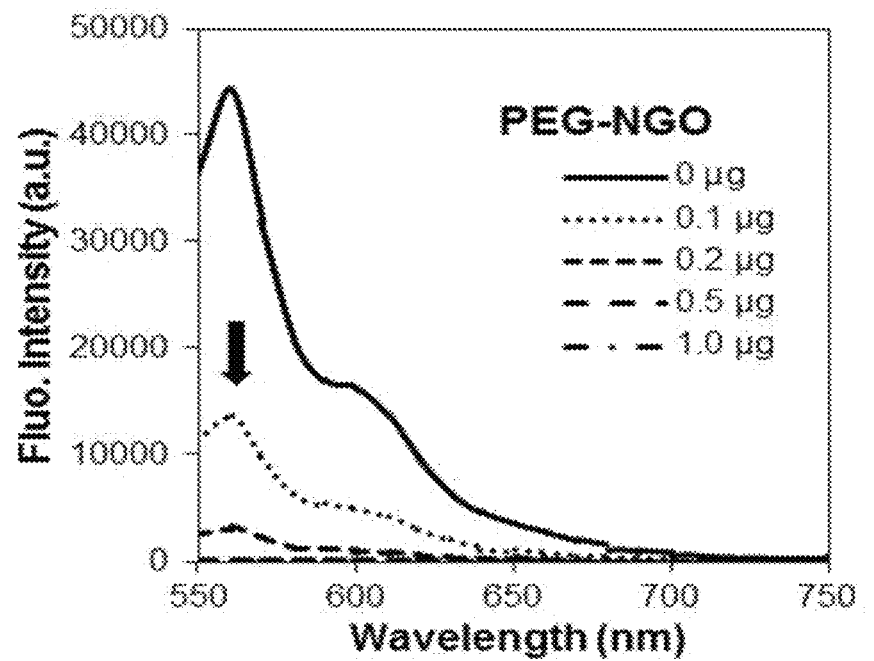

Experimental Example 1-3. Confirmation of Preparation of PEG-NGO Composition for Detecting Target Material To confirm whether the PEG-NGO prepared in Example 5 can be used as a composition for detecting a target material, an experiment was performed under the same conditions and in the same manner as in Experimental Example 1-1. Here, 10 pmol of a PNA probe was mixed with each of 0, 0.1, 0.2, 0.5 or 1.0 µg of PEG-NGO. As the PNA probe, one in which a Cy5 fluorescent dye is bound to PNA-Sa or PNA-Pa, listed in Table 1 below, was used. As a result, a value of the measured fluorescence signal is shown in FIGS. 8A and 8B. As shown in FIGS. 8A and 8B, a reduction in the fluorescence signal is dependent on a concentration of the added PNA probe, and therefore it was confirmed that the material forms a detection composition.

Figure 9:
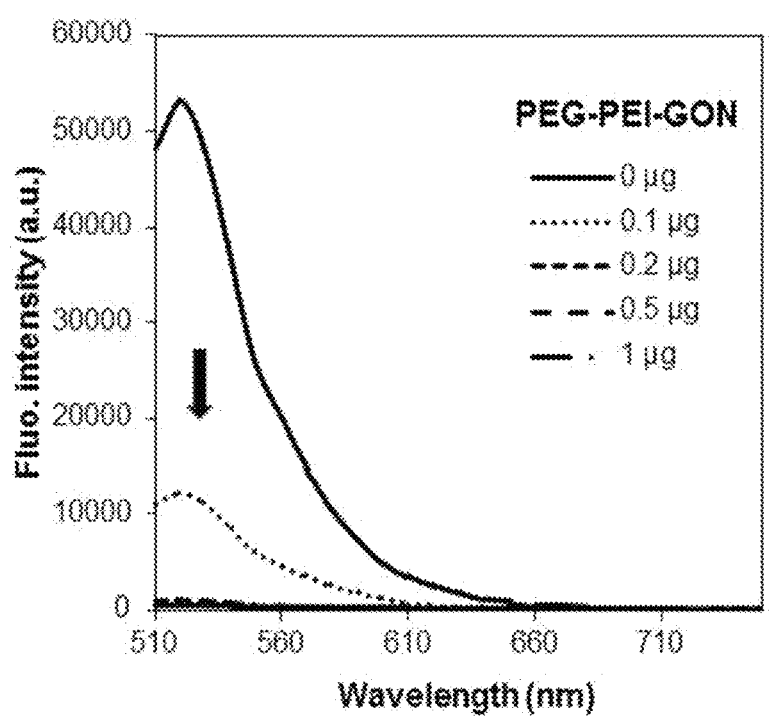
FIG. 9 is a graph representing a fluorescent signal emitted from a mixture of PEG-PEI-GON and PNA-TS as a probe, to confirm whether a detection composition is formed or not.

Experimental Example 1-4. Confirmation of Preparation of PEG-PEI-GON Composition for Detecting Target Material To confirm whether the PEG-PEI-GON prepared in Example 6 can be used as a composition for detecting a target material, an experiment was performed under the same conditions and in the same manner as in Experimental Example 1-1. 10 pmol of a PNA probe was mixed with each of 0, 0.1, 0.2, 0.5 or 1.0 µg of PEG-PEI-NGO. As the PNA probe, one in which an FITC fluorescent dye is bound to PNA-TS listed in Table 1 below was used. As a result, a value of the measured fluorescence signal is shown in FIG. 9. As shown in FIG. 9, a reduction in the fluorescence signal is dependent on a concentration of the added PNA probe, and therefore it was confirmed that the material forms a detection composition.

Experimental Example 2. Confirmation of Stability of DReGON Particles

Figure 10A:
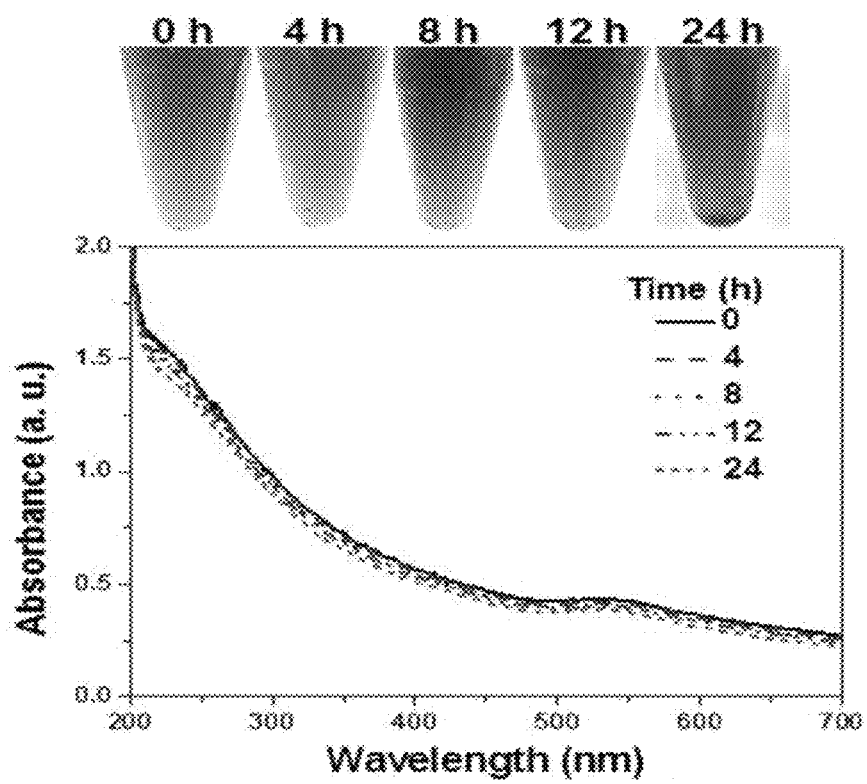
FIGS. 10A and 10B include diagrams for comparing the fluorescence stability of GON (FIG. 10A) with that of DReGON (FIG. 10B).
Figure 10B:
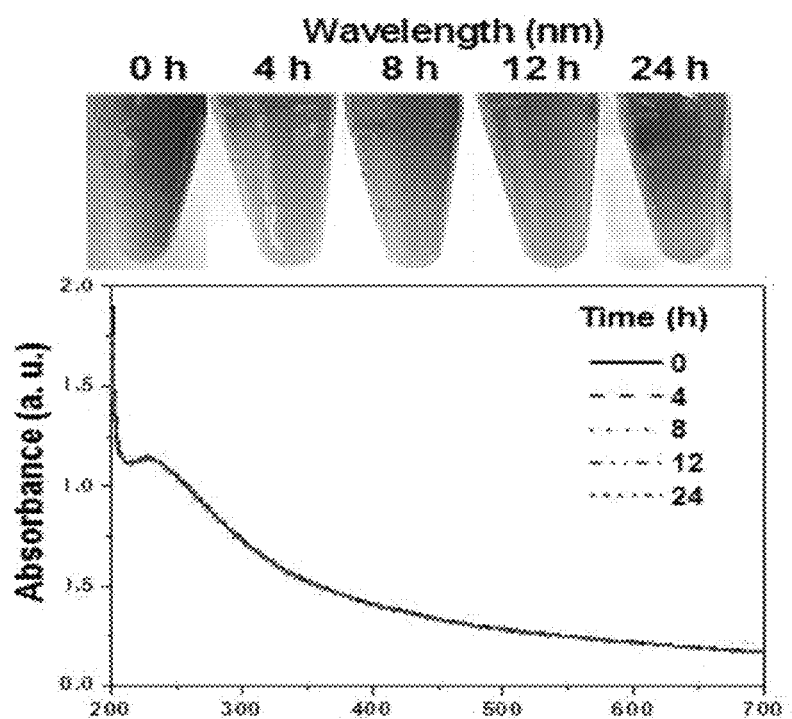

To confirm the stability of the DReGON particles prepared in Example 4, an experiment was carried out as follows. Specifically, 0.1 mg/ml of a DReGON solution was well suspended in a PBS solution containing serum, and maintained for 0, 4, 8, 12 or 24 hours at room temperature, followed by measurement of absorbance over time. As a control, the GON prepared in Example 1 was used. As a result, as shown in FIGS. 10A and 10B, DReGON (FIG. 10B) showed more stable absorption spectra in a physiologically active environment for a long period of time than those of GON (FIG. 10A), and such stable dispersibility was retained for 24 hours or longer.

IV. Confirmation of Target Material Detectability of Two-Dimensional Nanomaterial Surface-Modified with Polymer Experimental Example 3. Confirmation of Ability to Detect Cancer Cell-Specific Nucleic Acid Sequence Experimental Example 3-1. Confirmation of Detectability of DReGON To measure a detection limit of the DReGON prepared in Example 4, an experiment was carried out as follows. First, PNA21 and DReGON were mixed as probes and reacted under the same conditions and in the same manner as in Experimental Example 1-1. Thirty minutes after the reaction, a target material including a cancer cell-specific sequence, that is, miR-21, was added to the reaction product to have a concentration of 0, 0.001, 0.01, 0.1, 1, 10, 100 or 1,000 nM, and reacted at room temperature for 2 hours. Fluorescence signals were measured using a fluorescence reader at Ex/Em=647/670 nm. The sequences of the PNA probe and the target materials used in the experiment are listed in Tables 1 and 2 below.

TABLE 1

| Target disease | Probe | Sequence (5'→3') | SEQ ID NO: |
|---|---|---|---|
| Cancer | PNA21 | TCAACATCAGTCTGATAAGCTA | SEQ ID NO: 1 |
|  | PNA31 | AGCTATGCCAGCATCTTGCCT | SEQ ID NO: 2 |
|  | PNA223 | ATTTGACAAACTGAC | SEQ ID NO: 3 |
|  | PNA484 | GGAGGGGACTGAGCCTG | SEQ ID NO: 4 |
|  | Let-7a | AACTATACAACCTACTACCTCA | SEQ ID NO: 5 |
|  | PNA-TS | CTGCCCCAAAATGCCT | SEQ ID NO: 6 |
| Bacterial disease | PNA-Pa | GCGGCATGGCTGGATC | SEQ ID NO: 7 |
|  | PNA-Sa | ACAGAGTTTTACGATC | SEQ ID NO: 8 |
| Viral disease | PNA-US5-2 | AGACATCGTCACACCTATCATA | SEQ ID NO: 9 |
|  | PNA-DENV | GCGTTTCAGCATATTGA | SEQ ID NO: 10 |

TABLE 2

| Target disease | Target material | Sequence (5'→3') | SEQ ID NO: |
|---|---|---|---|
| Cancer | miR-21 | UAGCUUAUCAGACUGAUGUUGA | SEQ ID NO: 11 |
|  | miR-31 | AGGCAAGAUGCUGGCAUAGCU | SEQ ID NO: 12 |
|  | miR-223 | GUCAGUUUGUCAAAU | SEQ ID NO: 13 |
|  | miR-484 | CAGGCUCAGUCCCCUCC | SEQ ID NO: 14 |
|  | Let-7a | UGAGGUAGUAGGUUGUAUAGUU | SEQ ID NO: 15 |
|  | miR-TS | AGGCAUUUUGGGGCAG | SEQ ID NO: 16 |
| Bacterial disease | miR-Pa | GAUCCAGCCAUGCCGC | SEQ ID NO: 17 |
|  | miR-Sa | GAUCGUAAAACUCUGU | SEQ ID NO: 18 |
| Viral disease | miR-Us5-2 | UAUGAUAGGUGUGACGAUGUCU | SEQ ID NO: 19 |
|  | miR-DENV | UCAAUAUGCUGAAACGC | SEQ ID NO: 20 |

Figure 11:
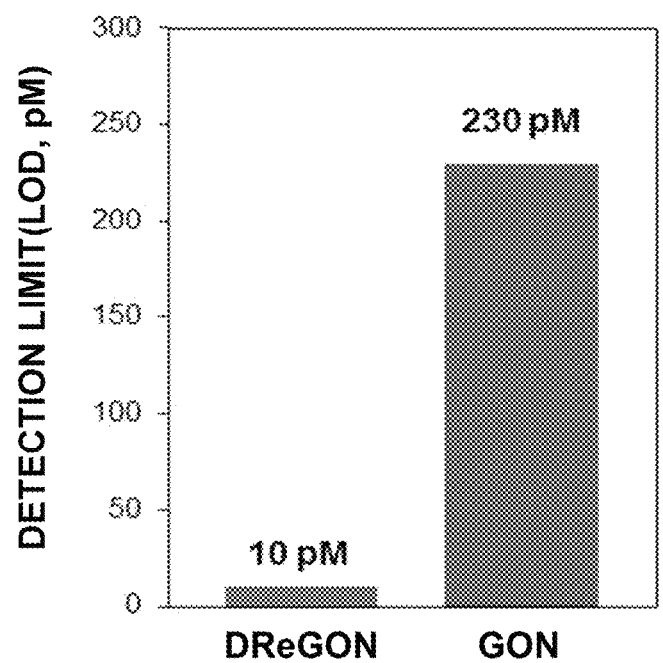
FIG. 11 is a graph for confirming the target material detection capability of DReGON and GON.

Results derived by substituting changes in fluorescence before and after the addition of a target material into Equation 1 below are shown in FIG. 11. Here, as a control, the GON prepared in Example 1 was used.

$$\text{Detection Limit} = 3.3\left(\frac{SD}{S}\right) \quad \text{[Equation 1]}$$

*SD: Standard deviation, S: Slope of calibration line

As shown in FIG. 11, GON detected up to 230 pM of the target material, but DReGON detected up to 10 pM of the target material. From the result, it was confirmed that the two-dimensional nanomaterial that was surface-modified with a polymer according to the present invention can also detect a target nucleic acid present at a low concentration in a sample.

Experimental Example 3-2. Confirmation of Detectability of PEG-NGO

Figure 12A:
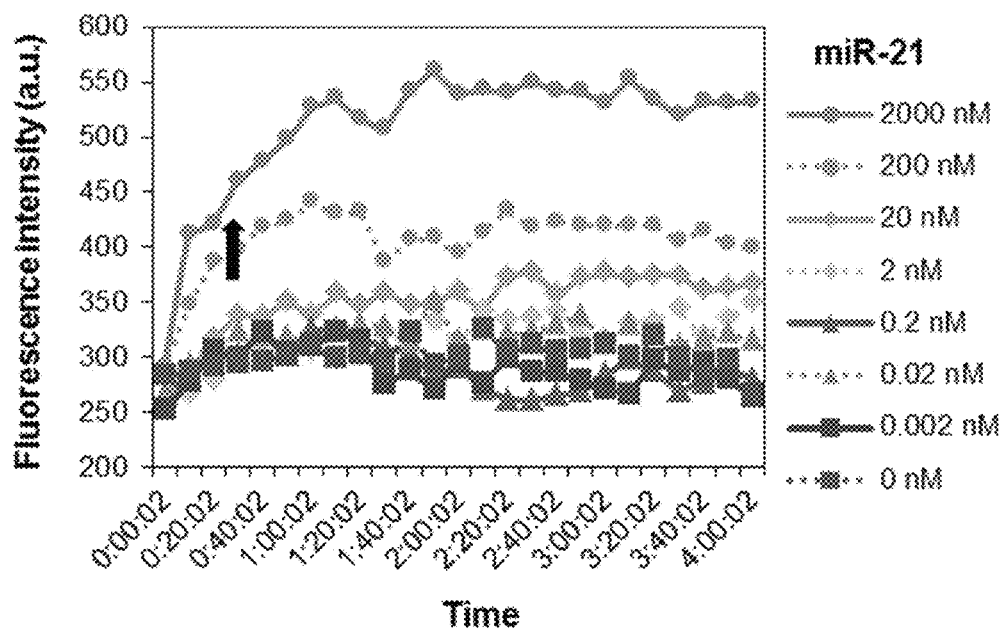
FIGS. 12A and 12B show that a graph for confirming the detection capability of PEG-NGO when miR-21 (FIG. 12A) or miR-223 (FIG. 12B) is added as a target material at various concentrations.
Figure 12B:
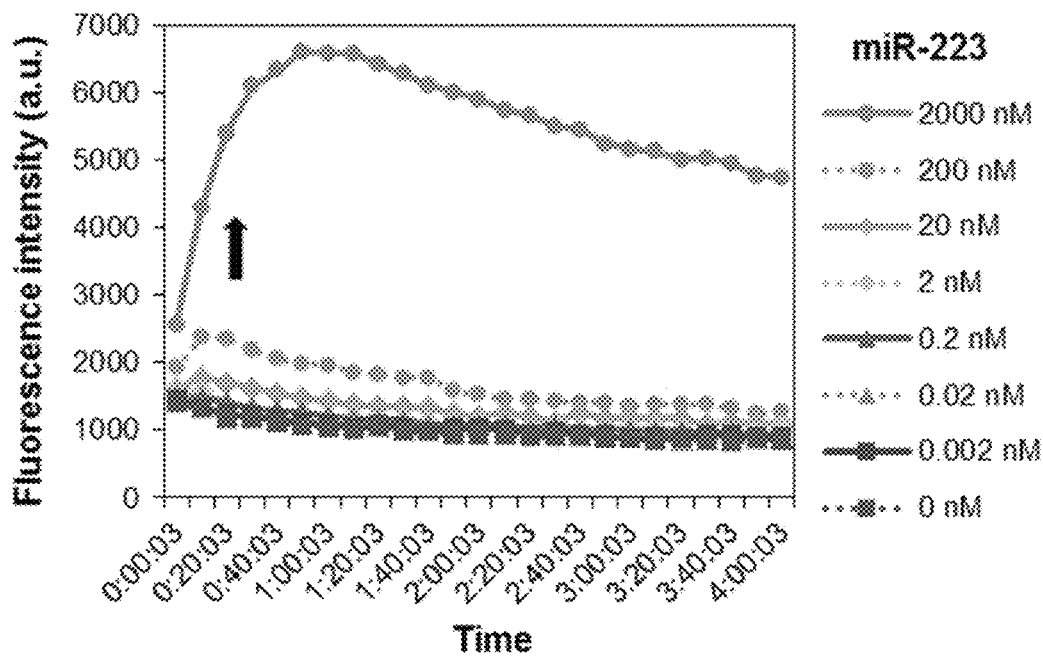

The ability of PEG-NGO to detect a cancer cell-specific nucleic acid sequence was confirmed under the same conditions and in the same manner as in Experimental Example 3-1. Here, 10 pmol of the PEG-NGO prepared in Example 5, instead of DReGON, was used, and PNA21 and PNA233 as probes and miR-21 and miR-233 as target materials were used at 0, 0.002, 0.02, 0.2, 2, 20, 200 or 2,000 nM. In addition, after the target material was added, a reaction was performed for 4 hours, a fluorescence change was measured at intervals of 20 minutes, and the result is shown in FIGS. 12A and 12B. As shown in FIGS. 12A and 12B, as the concentration of the target material was increased, the fluorescence signal became stronger, and fluorescence was restored to different levels according to the concentration and type of a probe.

Experimental Example 3-3. Confirmation of Detectability of PEG-PEI-GON

Figure 13:
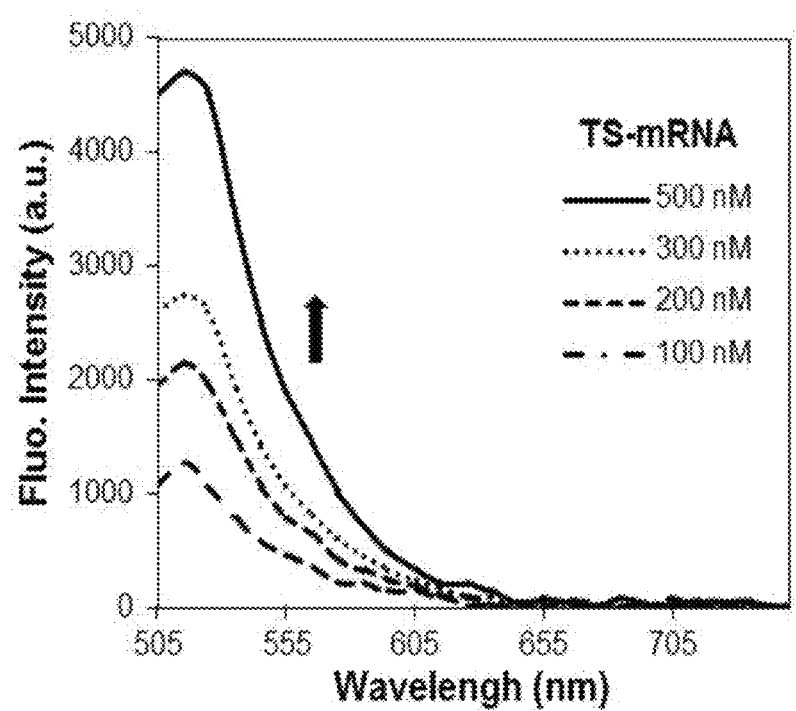
FIG. 13 is a graph for confirming the detection capability of PEG-PEI-GON when miR-TS is added as a target material at various concentrations.

The ability of PEG-PEI-NGO to detect a cancer cell-specific nucleic acid sequence was confirmed under the same conditions and in the same manner as in Experimental Example 3-1. Here, 10 pmol of the PEG-PEI-NGO prepared in Example 6, instead of DReGON, was used, and PNA-TS as a probe and miR-TS as a target material were used at 100, 200, 300 or 500 nM. In addition, after the target material was added, a reaction was performed for 4 hours, a fluorescence change was measured at intervals of 20 minutes, and the result is shown in FIG. 13. As shown in FIG. 13, as the concentration of the target material was increased, the fluorescence signal became stronger, and fluorescence was restored in a different level according to the concentration and type of a probe.

Experimental Example 3-4. Confirmation of Detectability of DReGON in Cancer Cell Lines The ability of DReGON to detect a cancer cell-specific nucleic acid sequence was confirmed using various types of cancer cell lines. First, MCF-7, HeLa and SW620 cell lines were prepared by being cultured in a DMEM or RPMI medium. However, PNA484 or PNA31 as a probe was mixed with DReGON under the same conditions and in the same manner as in Experimental Example 1-1 to allow a reaction. The prepared cells were seeded into a 12-well plate to have a density of 1×10⁵ cells per well, and after 24 hours, a reaction product of DReGON, and PNA484 or PNA31 was added to the cells at a concentration of 80 pmol.

Figure 14:
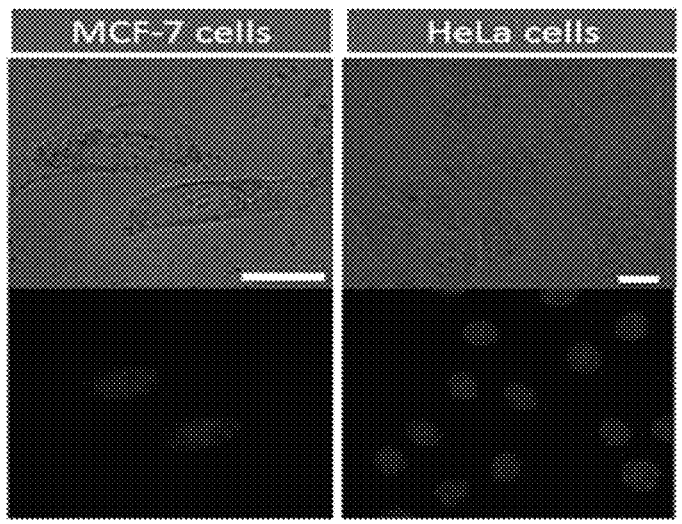
FIG. 14 includes images for confirming that no fluorescent signal is detected when a probe is not added to various cancer cell lines.
Figure 14:
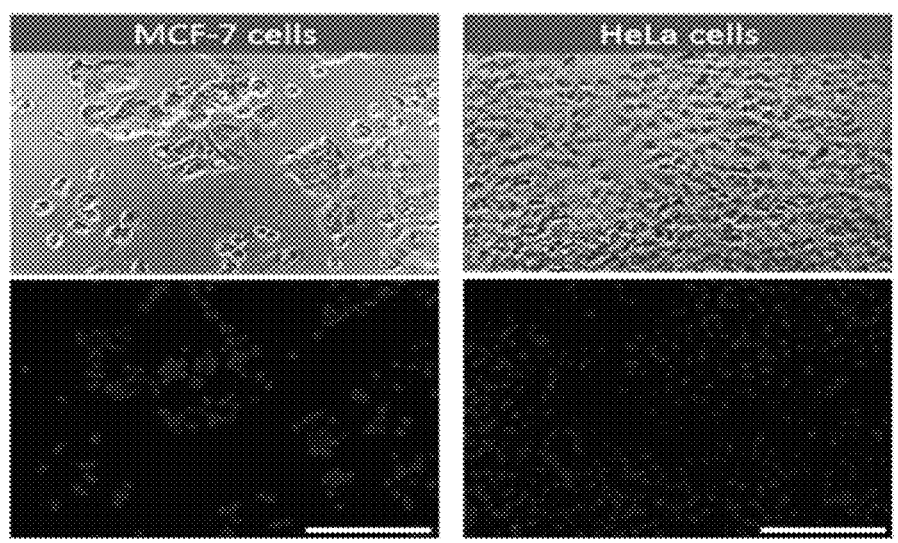
Figure 15:
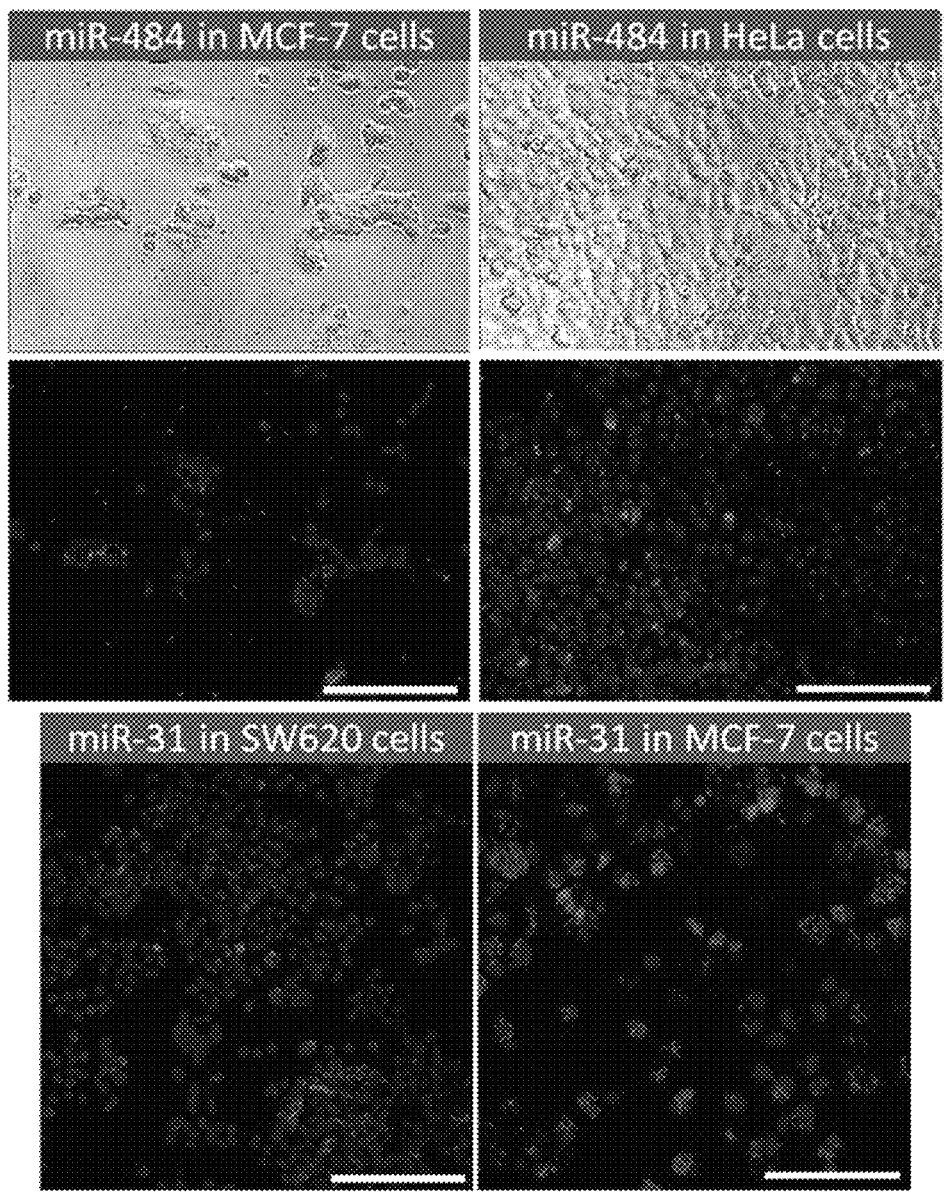
FIG. 15 includes images for confirming the cancer cell detection capability of DReGON mixed with PNA484 or PNA31 as a probe in various cancer cell lines.

After 14 hours, images of fluorescence signals of cells observed using a fluorescence microscope are shown in FIG. 15. Here, as a control, images taken without addition of a probe to cells are shown in FIG. 14. As shown in FIG. 15, detection of the target material by DReGON was identified through a fluorescence signal of a fluorescent material-conjugated probe.

Experimental Example 3-5. Confirmation of Detectability of DReGON in Blood Cells To confirm the detectability of DReGON for a specific base sequence present in blood cells, an experiment was carried out as follows. Specifically, blood cells were collected from 10 ml of healthy human blood by a known method, and cultured in an RPMI medium. The cultured cells were fixed and 200 nM of a PNA probe to which 3.0 μg of DReGON and a Cy5 fluorescent dye were bound was added. Here, as a PNA probe, PNA21, PNA223, Let-7a or a mixture thereof (scrambled) was used. As a control, an untreated cell group was used.

Figure 16A:
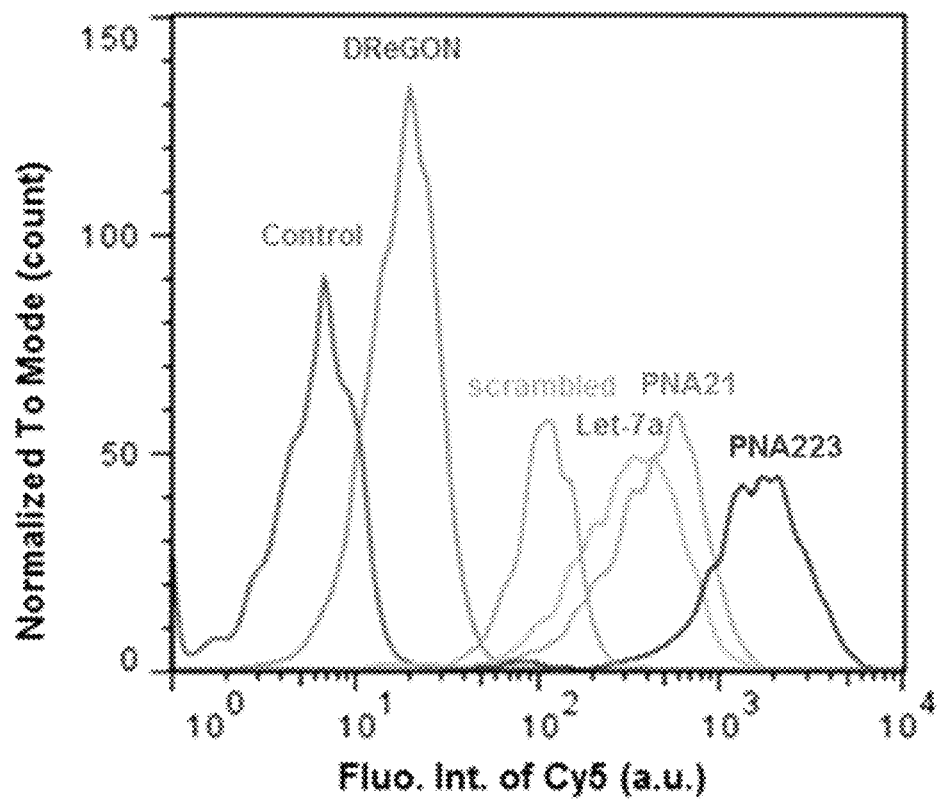
FIGS. 16A and 16B include graphs for confirming the blood cell detection capability of DReGON mixed with PNA21, PNA223, Let-7a or a mixture thereof (scrambled) as a probe.
Figure 16B:
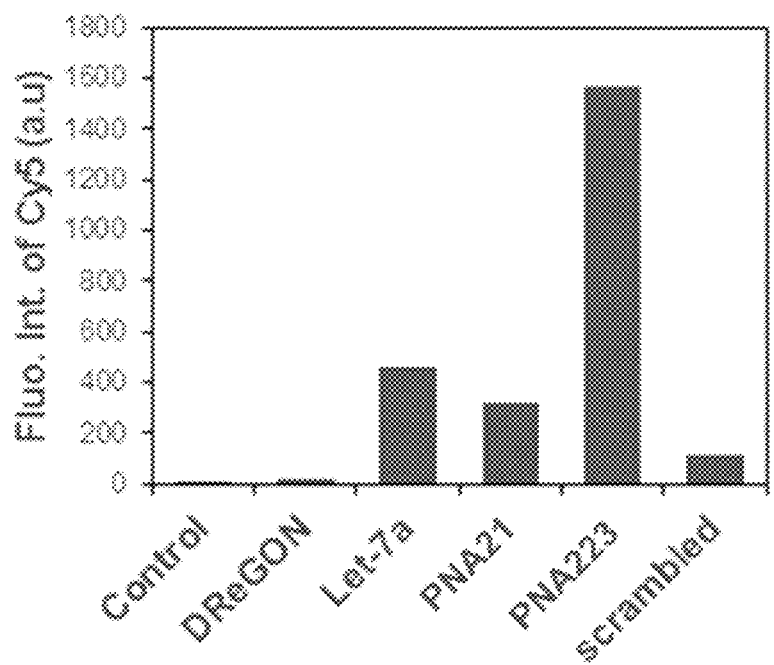

After 4 hours, the intensity of fluorescence restored in the blood cells, detected by flow cytometry, is shown in FIGS. 16A and 16B. As shown in FIGS. 16A and 16B, it was confirmed that a target base sequence expressed in the blood cells is detected by the PNA probe.

Figure 17A:
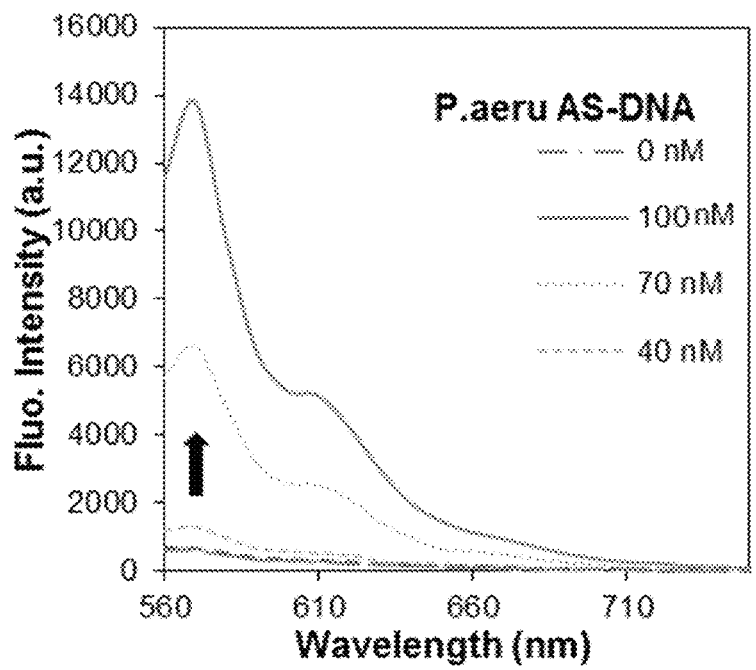
FIGS. 17A and 17B are graphs of fluorescence levels shown after various concentrations of a fluorescence-labeled nucleic acid sequence specifically binding to *Pseudomonas aeruginosa* (FIG. 17A) or *Staphylococcus aureus* (FIG. 17B) are mixed with PEG-NGO, and mixed with *Pseudomonas aeruginosa* or *Staphylococcus aureus*.
Figure 17B:
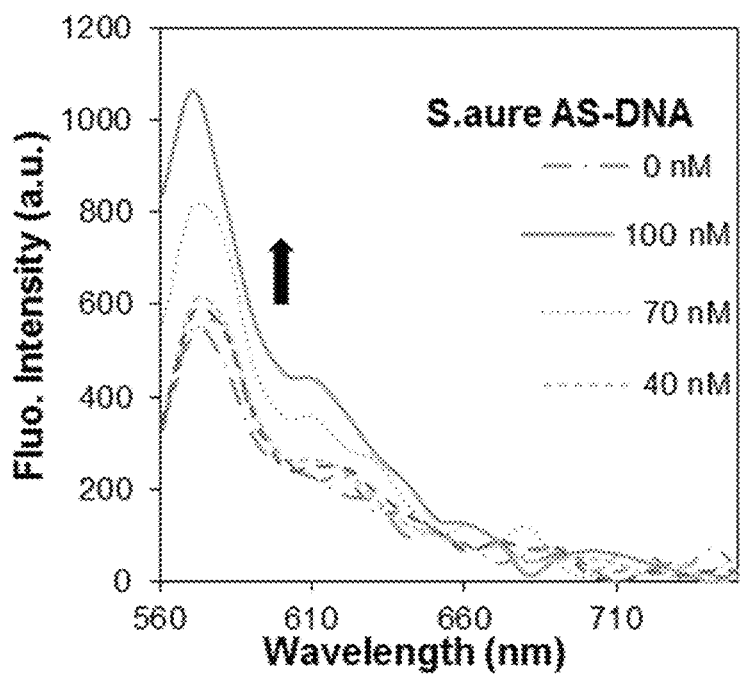

Experimental Example 4. Confirmation of Ability of PEG-NGO to Detect Bacteria-Specific Nucleic Acid Sequence The ability of PEG-NGO to detect a *Pseudomonas aeruginosa* or *Staphylococcus aureus*-specific nucleic acid sequence was confirmed under the same conditions and in the same manner as in Experimental Example 3-1. Here, 0.2 μg of the PEG-NGO prepared in Example 5, instead of DReGON, and 10 pmol of PNA-Pa or PNA-Sa were added, and then 0, 10, 20, 40, 70 or 100 nM of *Pseudomonas aeruginosa* or *Staphylococcus aureus* AS-DNA was added thereto as a target material. As a result, the measured fluorescence change is shown in FIGS. 17A and 17B. As shown in FIGS. 17A and 17B, the intensity of fluorescence was increased depending on the concentration of the added *Pseudomonas aeruginosa* or *Staphylococcus aureus* AS-DNA.

Figure 18A:
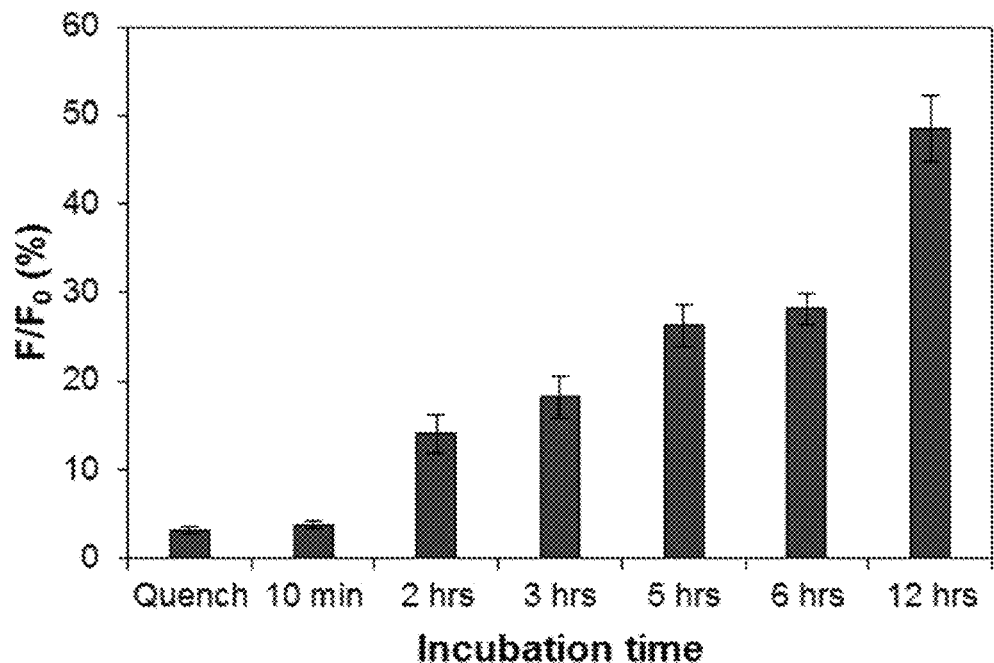
FIGS. 18A and 18B are graphs of fluorescence levels shown after a nucleic acid sequence specifically binding to human cytomegalovirus (FIG. 18A) or dengue virus (FIG. 18B) is mixed with DReGON, and mixed with human cytomegalovirus or dengue virus.
Figure 18B:
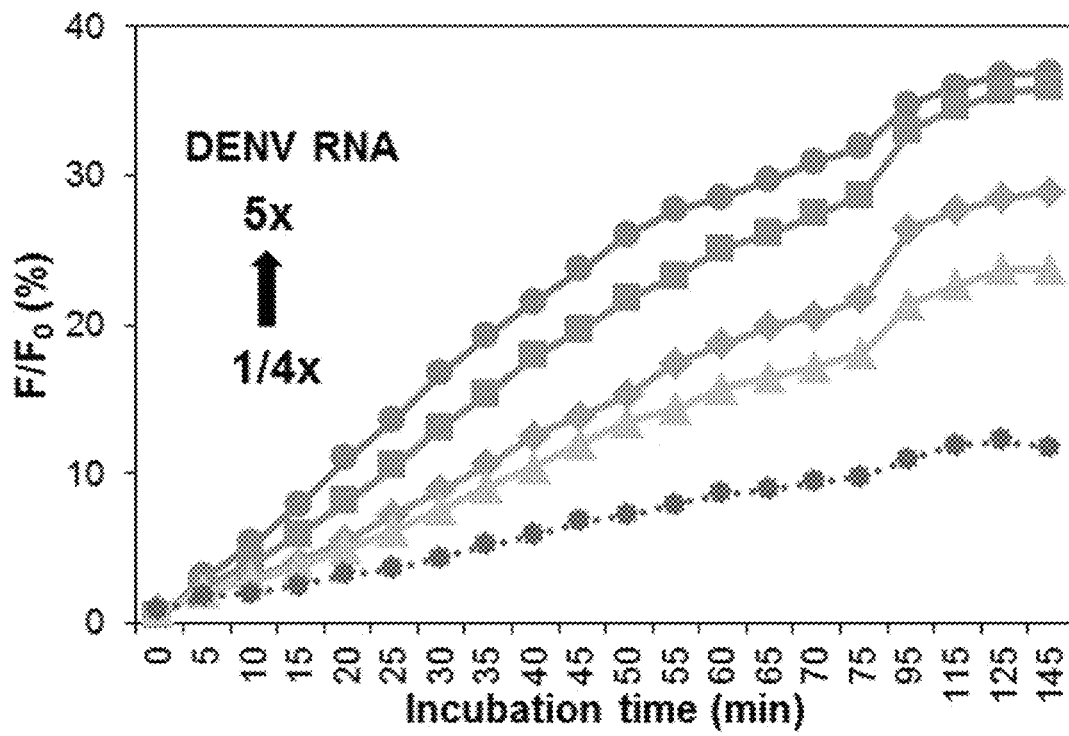

Experimental Example 5. Confirmation of Ability DReGON to Detect Virus-Specific Nucleic Acid Sequence The ability of DReGON to detect a human cytomegalovirus (HCMV) or dengue virus (DENV)-specific nucleic acid sequence was confirmed under the same conditions and in the same manner as in Experimental Example 3-1. Here, 0.5 μg of DReGON, and 20 pmol of PNA-US5-2 or PNA-DENV were added, and 20 pmol of miR-US5-2 or miR-DENV was added thereto as a target material. As a result, fluorescence changes measured over reaction time are shown in FIGS. 18A and 18B. As shown in FIGS. 18A and 18B, the intensity of fluorescence for a HCMV or DENV-specific nucleic acid sequence added depending on a reaction time was increased.

Consequently, from the results, it can be demonstrated that, unlike a microarray or RT-PCR, the composition of the present invention can easily detect a target sequence, and can be used to indirectly confirm the concentration of the target sequence.

| Sequence Listing Free Text |
|---|
| SEQ ID NO: 1: tcaacatcag tctgataagc ta |
| SEQ ID NO: 2: agctatgcca gcatcttgcc t |
| SEQ ID NO: 3: atttgacaaa ctgac |
| SEQ ID NO: 4: ggaggggact gagcctg |
| SEQ ID NO: 5: aactatacaa cctactacct ca |
| SEQ ID NO: 6: ctgccccaaa atgcct |
| SEQ ID NO: 7: gcggcatggc tggatc |
| SEQ ID NO: 8: acagagtttt acgatc |
| SEQ ID NO: 9: agacatcgtc acacctatca ta |
| SEQ ID NO: 10: gcgtttcagc atattga |
| SEQ ID NO: 11: uagcuuauca gacugauguu ga |
| SEQ ID NO: 12: aggcaagaug cuggcauagc u |
| SEQ ID NO: 13: gucaguuugu caaau |
| SEQ ID NO: 14: caggcucagu ccccucc |
| SEQ ID NO: 15: ugagguagua gguuguauag uu |
| SEQ ID NO: 16: aggcauuuug gggcag |
| SEQ ID NO: 17: gauccagcca ugccgc |
| SEQ ID NO: 18: gaucguaaaa cucugu |
| SEQ ID NO: 19: uaugauaggu gugacgaugu cu |
| SEQ ID NO: 20: ucaauaugcu gaaacgc |

The invention claimed is:

1. A composition comprising:
a graphene oxide nanocolloid (GON);
a water-soluble polymer bound to a carboxylic group moiety on a surface of the GON; and
a fluorescent material-conjugated probe bound to a surface where the water-soluble polymer is not bonded of the GON,
wherein the water-soluble polymer is selected from the group consisting of chitosan, a derivative of the chitosan, a chitosan salt, dextran, a derivative of dextran, hyaluronic acid, a derivative of hyaluronic acid, a hyaluronate, pectin, a derivative of hyaluronate, pectin, a pectin salt, an alginate, a derivative of alginate, alginic acid, agar, a galactomannan, a derivative of galactomannan, a galactomannan salt, xanthan, a derivative of xanthan, a xanthan salt, β-cyclodextrin, a derivative of β-cyclodextrin, a β-cyclodextrinate, polyethylene glycol (PEG), polyethyleneimine (PEI), and a combination thereof.

2. The composition of claim 1, wherein the GON has a particle size of 0.01 to 1 μm.

3. The composition of claim 1, wherein the polymer is bound by a chemical or physical bond.

4. The composition of claim 3, wherein the chemical bond is EDC coupling.

5. The composition of claim 3, wherein the physical bond is a hydrogen bond.

6. The composition of claim 1, wherein the probe is any one selected from the group consisting of an antibody, a nucleic acid, a peptide, a protein and a combination thereof.

7. The composition of claim 6, wherein the nucleic acid consists of 10 to 50 bases.

8. The composition of claim 6, wherein the nucleic acid is any one selected from the group consisting of DNA, RNA, mRNA, miRNA, non-coding RNA, double helix RNA, double helix DNA, a DNA-based enzyme, a deoxyribozyme, an aptamer, a peptide nucleic acid (PNA), a locked nucleic acid (LNA) and a combination thereof.

9. The composition of claim 6, wherein the nucleic acid is any one selected from the group consisting of SEQ ID NOs: 1 to 10.

10. The composition of claim 1, wherein the fluorescent material is selected from the group consisting of fluorescein, fluorescein chlorotriazinyl, rhodamine green, rhodamine red, tetramethylrhodamine, fluorescein isothiocyanate (FITC), Oregon green, an Alex Fluor dye, carboxyfluorescein (FAM), 6-carboxy-4',5'-dichloro-2',7'-dimethoxyfluorescein (JOE), carboxy-X-rhodamine (ROX), 6-carboxy-2',4,4',5',7,7'-hexachlorofluorescein (HEX), Texas red (sulforhodamine 101 acid chloride), 6-carboxy-2',4,7',7-tetrachlorofluorescein (TET), tetramethylrhodamine-isothiocyanate (TRITC), carboxytetramethylrhodamine (TAMRA), a cyanine-based dye, a thiodicarbocyanine dye, and a combination thereof.

11. The composition of claim 10, wherein the cyanine-based dye is any one selected from the group consisting of Cy3, CyS, Cy5.5, Cy7 and a combination thereof.

12. The composition of claim 1, wherein the composition is for detection of a biomaterial or diagnosis of a disease.

13. The composition of claim 12, wherein the disease is cancer, an infectious disease, an inflammatory disease, or a genetic disease.

14. The composition of claim 13, wherein the infectious disease is caused by an infection of any one selected from the group consisting of bacteria, fungi, viruses, parasites and a combination thereof.

15. The composition of claim 14, wherein the bacteria include any one selected from the group consisting of *Pseudomonas aeruginosa, Staphylococcus aureus, Acinetobacter baumannii* and a combination thereof.

16. The composition of claim 14, wherein the viruses include any one selected from the group consisting of a double-stranded DNA virus, a single-stranded DNA virus, a double-stranded RNA virus, a positive-sense single-stranded RNA virus, a negative-sense single-stranded RNA virus, a single-stranded RNA retrovirus, a double-stranded DNA retrovirus and a combination thereof.

17. The composition of claim 14, wherein the virus is any one selected from the group consisting of human cytomegalovirus, Dengue virus and a combination thereof.

18. A method for providing information necessary for the diagnosis of a disease, comprising:
  1) mixing the composition of claim 1 with an isolated sample;
  2) measuring a fluorescence level of the mixture; and
  3) comparing the resulting level with a fluorescence level of a normal control sample.

19. The method of claim 18, wherein the disease is cancer, an infectious disease, an inflammatory disease or a genetic disease.

20. A kit comprising the composition of claim 1.

* * * * *

UNITED STATES PATENT AND TRADEMARK OFFICE
CERTIFICATE OF CORRECTION

PATENT NO. : 10,809,196 B2
APPLICATION NO. : 15/765409
DATED : October 20, 2020
INVENTOR(S) : Cheolhee Won et al.

Page 1 of 1

It is certified that error appears in the above-identified patent and that said Letters Patent is hereby corrected as shown below:

On the Title Page

Update item (12) to read as follows:
(12) Cheolhee WON

The inventorship should be corrected to read as below:
Cheolhee WON, Seoul (KR)

Signed and Sealed this
Seventh Day of March, 2023

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: PNA21

<400> SEQUENCE: 1
tcaacatcag tctgataagc ta                                            22

<210> SEQ ID NO 2
<211> LENGTH: 21
<212> TYPE: DNA
<213> ORGANISM: Artificial Sequence
<220> FEATURE:
<223> OTHER INFORMATION: PNA31

<400> SEQUENCE: 2
agctatgcca gcatcttgcc t                                             21

<210> SEQ ID NO 3
<211> LENGTH: 15
<212> TYPE: DNA
<213> ORGANISM: Artificial Sequence
<220> FEATURE:
<223> OTHER INFORMATION: PNA223

<400> SEQUENCE: 3
atttgacaaa ctgac                                                    15

<210> SEQ ID NO 4
<211> LENGTH: 17
<212> TYPE: DNA
<213> ORGANISM: Artificial Sequence
<220> FEATURE:
<223> OTHER INFORMATION: PNA484

<400> SEQUENCE: 4
ggaggggact gagcctg                                                  17

<210> SEQ ID NO 5
<211> LENGTH: 22
<212> TYPE: DNA
<213> ORGANISM: Artificial Sequence
<220> FEATURE:
<223> OTHER INFORMATION: Let-7a

<400> SEQUENCE: 5
aactatacaa cctactacct ca                                            22

<210> SEQ ID NO 6
<211> LENGTH: 16
<212> TYPE: DNA
<213> ORGANISM: Artificial Sequence
<220> FEATURE:
<223> OTHER INFORMATION: PNA-TS

<400> SEQUENCE: 6
ctgccccaaa atgcct                                                   16

<210> SEQ ID NO 7
<211> LENGTH: 16
<212> TYPE: DNA
<213> ORGANISM: Artificial Sequence
<220> FEATURE:
<223> OTHER INFORMATION: PNA-Pa

<400> SEQUENCE: 7
gcggcatggc tggatc                                                   16

<210> SEQ ID NO 8
<211> LENGTH: 16
<212> TYPE: DNA

```
<213> ORGANISM: Artificial Sequence
<220> FEATURE:
<223> OTHER INFORMATION: PNA-Sa

<400> SEQUENCE: 8
acagagtttt acgatc                                                        16

<210> SEQ ID NO 9
<211> LENGTH: 22
<212> TYPE: DNA
<213> ORGANISM: Artificial Sequence
<220> FEATURE:
<223> OTHER INFORMATION: PNA-US5-2

<400> SEQUENCE: 9
agacatcgtc acacctatca ta                                                 22

<210> SEQ ID NO 10
<211> LENGTH: 17
<212> TYPE: DNA
<213> ORGANISM: Artificial Sequence
<220> FEATURE:
<223> OTHER INFORMATION: PNA-DENV

<400> SEQUENCE: 10
gcgtttcagc atattga                                                       17

<210> SEQ ID NO 11
<211> LENGTH: 22
<212> TYPE: RNA
<213> ORGANISM: Artificial Sequence
<220> FEATURE:
<223> OTHER INFORMATION: miR-21

<400> SEQUENCE: 11
uagcuuauca gacugauguu ga                                                 22

<210> SEQ ID NO 12
<211> LENGTH: 21
<212> TYPE: RNA
<213> ORGANISM: Artificial Sequence
<220> FEATURE:
<223> OTHER INFORMATION: miR-31

<400> SEQUENCE: 12
aggcaagaug cuggcauagc u                                                  21

<210> SEQ ID NO 13
<211> LENGTH: 15
<212> TYPE: RNA
<213> ORGANISM: Artificial Sequence
<220> FEATURE:
<223> OTHER INFORMATION: miR-223

<400> SEQUENCE: 13
gucaguuugu caaau                                                         15

<210> SEQ ID NO 14
<211> LENGTH: 17
<212> TYPE: RNA
<213> ORGANISM: Artificial Sequence
<220> FEATURE:
<223> OTHER INFORMATION: miR-484

<400> SEQUENCE: 14
caggcucagu ccccucc                                                       17
```

```
<210> SEQ ID NO 15
<211> LENGTH: 22
<212> TYPE: RNA
<213> ORGANISM: Artificial Sequence
<220> FEATURE:
<223> OTHER INFORMATION: Let-7a

<400> SEQUENCE: 15
ugagguagua gguuguauag uu                                              22

<210> SEQ ID NO 16
<211> LENGTH: 16
<212> TYPE: RNA
<213> ORGANISM: Artificial Sequence
<220> FEATURE:
<223> OTHER INFORMATION: miR-TS

<400> SEQUENCE: 16
aggcauuuug gggcag                                                     16

<210> SEQ ID NO 17
<211> LENGTH: 16
<212> TYPE: RNA
<213> ORGANISM: Artificial Sequence
<220> FEATURE:
<223> OTHER INFORMATION: miR-Pa

<400> SEQUENCE: 17
gauccagcca ugccgc                                                     16

<210> SEQ ID NO 18
<211> LENGTH: 16
<212> TYPE: RNA
<213> ORGANISM: Artificial Sequence
<220> FEATURE:
<223> OTHER INFORMATION: miR-Sa

<400> SEQUENCE: 18
gaucguaaaa cucugu                                                     16

<210> SEQ ID NO 19
<211> LENGTH: 22
<212> TYPE: RNA
<213> ORGANISM: Artificial Sequence
<220> FEATURE:
<223> OTHER INFORMATION: miR-US5-2

<400> SEQUENCE: 19
uaugauaggu gugacgaugu cu                                              22

<210> SEQ ID NO 20
<211> LENGTH: 17
<212> TYPE: RNA
<213> ORGANISM: Artificial Sequence
<220> FEATURE:
<223> OTHER INFORMATION: miR-DENV

<400> SEQUENCE: 20
ucaauaugcu gaaacgc                                                    17
```